US008101201B2

(12) United States Patent
Artisa et al.

(10) Patent No.: US 8,101,201 B2
(45) Date of Patent: *Jan. 24, 2012

(54) COMPOSITIONS COMPRISING DIETARY FAT COMPLEXER AND METHODS FOR THEIR USE

(75) Inventors: Joseph D Artisa, Windsor (CA); Catherine Jen, Bloomfield Hills, MI (US)

(73) Assignee: ArtJen Complexus, Inc., Windsor (CA)

( * ) Notice: Subject to any disclaimer, the term of this patent is extended or adjusted under 35 U.S.C. 154(b) by 1054 days.

This patent is subject to a terminal disclaimer.

(21) Appl. No.: 10/923,000

(22) Filed: Aug. 23, 2004

(65) Prior Publication Data

US 2005/0019375 A1  Jan. 27, 2005

Related U.S. Application Data

(63) Continuation of application No. 10/628,475, filed on Jul. 29, 2003, now Pat. No. 6,890,549.

(60) Provisional application No. 60/486,440, filed on Jul. 14, 2003, provisional application No. 60/461,847, filed on Apr. 11, 2003, provisional application No. 60/404,366, filed on Aug. 19, 2002.

(51) Int. Cl.
*A61K 47/00* (2006.01)
*A23D 7/00* (2006.01)

(52) U.S. Cl. .......................... 424/439; 426/601; 426/611

(58) Field of Classification Search .................. 424/439; 426/601, 611
See application file for complete search history.

(56) References Cited

U.S. PATENT DOCUMENTS

| 4,880,573 | A | * | 11/1989 | Courregelongue et al. .... | 426/417 |
| 5,189,149 | A | * | 2/1993 | Bruzzese et al. ................ | 514/58 |
| 5,198,250 | A | * | 3/1993 | Brillhart et al. ................... | 426/2 |
| 5,217,734 | A | | 6/1993 | Tanaka | |
| 5,232,725 | A | | 8/1993 | Roderbourg et al. | |
| 5,264,226 | A | | 11/1993 | Graille et al. | |
| 5,264,241 | A | | 11/1993 | Graille et al. | |
| 5,532,009 | A | | 7/1996 | Fortier | |
| 5,560,950 | A | * | 10/1996 | Conte et al. ................ | 426/330.6 |
| 5,571,554 | A | | 11/1996 | Dressnandt et al. | |
| 5,709,888 | A | * | 1/1998 | Gil et al. ........................ | 424/522 |
| 5,738,898 | A | | 4/1998 | Smith et al. | |
| 5,780,096 | A | | 7/1998 | Tanaka | |
| 5,824,354 | A | | 10/1998 | Ritter et al. | |
| 5,880,095 | A | * | 3/1999 | Park et al. ........................ | 514/12 |

(Continued)

FOREIGN PATENT DOCUMENTS

EP   1 120 046 A1   1/2001

(Continued)

OTHER PUBLICATIONS

Google search for Saponin, © 2006.*

(Continued)

*Primary Examiner* — Blessing Fubara

(74) *Attorney, Agent, or Firm* — Crowell & Moring LLP

(57) ABSTRACT

This invention relates to fat containing consumable food products comprising α-cyclodextrin. The food products have reduced levels of bioavailable fat but have substantially the same fat, cholesterol and caloric content as a like food without α-cyclodextrin. The invention also relates to methods for reducing the bioavailability of fats in fat containing food products without reducing caloric intake as determined by bomb calorimetry and to methods for increasing high density lipoproteins in a subject and reducing or controlling weight by administering the food products of this invention.

5 Claims, 8 Drawing Sheets

U.S. PATENT DOCUMENTS

| | | | |
|---|---|---|---|
| 5,894,029 A | | 4/1999 | Brown et al. |
| 5,965,449 A | * | 10/1999 | Novak .......................... 436/71 |
| 5,989,583 A | | 11/1999 | Amselem |
| 6,129,945 A | | 10/2000 | Awad et al. |
| 2003/0190402 A1 | * | 10/2003 | McBride ...................... 426/601 |

FOREIGN PATENT DOCUMENTS

| | | | | |
|---|---|---|---|---|
| JP | 52010448 | | | 1/1977 |
| JP | 60-049752 | | | 3/1985 |
| JP | 6094912 | | * | 5/1985 |
| JP | 60094912 | | | 5/1985 |
| JP | 62011072 | | * | 1/1987 |
| JP | 60-219720 | | | 4/1987 |
| JP | 2-261334 | | | 10/1990 |
| JP | 4-237477 | A | | 8/1992 |
| JP | 06153860 | | * | 6/1994 |
| JP | 6153861 | | | 6/1994 |
| JP | 6-269256 | | * | 9/1994 |
| JP | 8-269256 | A | | 9/1994 |
| JP | 06-343419 | | * | 12/1994 |
| JP | 05164024 | | | 12/1994 |
| JP | 06343419 | | * | 12/1994 |
| JP | 7115934 | | | 5/1995 |
| JP | 7115935 | | | 5/1995 |
| JP | 05113603 | | | 7/1996 |
| JP | 08187060 | | * | 7/1996 |
| JP | 2002306119 | | * | 10/2002 |

OTHER PUBLICATIONS

Medical Terminology and Drug Data Base for saponin © 2006; search via Google.*
Abadie et al. "Effect of cyclodextrins and undigested starch on the loss of chenodeoxycholate in the faeces." Biochem J. 1:299(3) (1994): 725-30. (Abstract).
Boehler et al. "Antilithiasic effect of beta-cyclodextrin in LPN hamster: comparison with cholestyramine." J. Lipid Res. 40:4 (1999): 726-34. (Abstract).
Favier et al. "Effect of cyclodextrin on plasma lipids and cholesterol metabolism in the rat." Metabolism 44:2 (1995): 200-6. (Abstract).
Favier et al. "Fermentable carbohydrates exert a more potent cholesterol-lowering effect than cholestryramine." Biochim Biophys.Act 1258:2 (1995): 115-21. (Abstract).
Ferezou et al. "Hypocholesterolemic action of beta-cyclodextrin and its effects on cholesterol metabolism in pigs fed a cholesterol-enriched diet." J. Lipid Res. 38:1 (1997): 86-100. (Abstract).
Lach J.L. "Interaction of pharmaceuticals with Schardinger dextrins. VI. Interactions of beta-cyclodextrin, sodium deoxycholate, and deoxycholic acid with amines and pharmaceutical agents." J. Pharm. Sci. 55:1 (1966): 32-8.
Moundras, C. "Fermentable polysaccharides that enhance fecal bile acid excretion lower plasma cholesterol and apoliprotein E-rich HDL in rats." J. Nutr. 124:11 (1994): 2179-88. (Abstract).
Trautwein et al. Impact of beta-cyclodextim and resistant starch on bile acid metabolism and fecal steroid excretion in regard to their hypolipidemic action in hamsters. Biochim Biophys. Acta. 1437:1 (1999): 1-12. (Abstract).
Oppeneer, Todd and Jarvi, Erin M., "Final Report—Determination of the Effects of a Fat Blocker on the Apparent Fat Digestibility and Serum Lipid Concentrations in Minipig Swine", Covance Laboratories, Inc., Apr. 29, 2004, pp. 1-74.
G. H. Anderson, et al., "The Utilization of Schardinger Dextrins by the Rat", Toxicology and Applied Pharmacology, 1963, pp. 257-266.
Kazuko Shimada, et al., "Structure of Inclusion Complexes of Cyclodextrins with Triglyceride at Vegetable Oil/Water Interface", Journal of Food Science, vol. 7, 1992, pp. 655-656.
Masashige Suzuki, et al., "Nutritional Significance of Cyclodextrins: Indigestibility and Hypolipemic Effect of α-Cyclodextrin", J. Nutr. Sci. Vitaminol. 31, 1985. 209-223.
Sarunya Kaewprasert, et al., "Nutritional Effects of Cyclodextrins on Liver and Serum Lipids and Cecal Organic Acids in Rats", J. Nutr. Sci. Vitaminol. 47, pp. 335-339.
Jozsef Szejtli, "Utilization of Cyclodextrins in Industrial Products and Processes", J. Mater. Chem., 1997, pp. 575-587.
Catherine Jen, Ph.D, et al., "Lipid Lowering Effect of Omega-3 Fatty Acids in Genetically Obese Zucker Rats", Nutrition Research, vol. 9, 1989. pp. 1217-1228.
Ryozo Takada, et al. "Dietary γ-Linolenic Acid-Enriched Oil Reduces Body Fat Content and Induces Liver Enzyme Activities relating to Fatty Acid β-Oxidation in Rats", American Institute of Nutrition, Nov. 15, 1993.
Raben, et al., "Acetylation of or Beta-Cyclodextrin Addition to Potato Starch Beneficial Effect on Glucose Metabolism and Appetite Sensations", Am J Clin Nutr, 66(2): 304-14, 1997.
Yuan, et al., Application of Molecular Encapsulation for Toxicology Studies: Toxicokinetics of p-chloro-alpha, alpha, alpha-trifluorotoluene in alpha-cyciodextrin or corn oil vehicles in male F344 rats, Toxicol Appl Pharmacol. 111(1): 107-15, 1991.
Szejtli, J., Utilization of Cyclodextrins In Industrial Products and Processes, Journal of Materials Chemistry, The Royal Society of Chemistry, Cambridge, GB, Apr. 4, 1997, vol. 7, No. 4, pp. 575-587, XP 000657743.
Supplementary European Search Report dated Jul. 9, 2007 (in English), Six (6) pages total.

* cited by examiner

COMPOSITIONS COMPRISING DIETARY FAT COMPLEXER AND METHODS FOR THEIR USE

This application is a continuation of U.S. application Ser. No. 10/628,475 filed Jul. 29, 2003 now U.S. Pat. No. 6,890,549 which claims priority to U.S. provisional patent applications Ser. No. 60/486,440 filed Jul. 14, 2003, Ser. No. 60/461,847 filed Apr. 11, 2003 and Ser. No. 60/404,366 filed Aug. 19, 2002 all incorporated herein in their entirety.

FIELD OF THE INVENTION

This invention relates to consumable products, particularly fat-containing consumable products, comprising α-cyclodextrin and methods of their use. The invention also relates to methods of reducing the bioavailability of fats in fat containing consumable products and to methods for enhancing organoleptic properties of fat containing consumable products.

BACKGROUND OF THE INVENTION

Efforts to control body weight through diet, exercise and drugs have met with only limited success. Obesity continues to be of epidemic proportions in the USA. It was estimated that in 2000, more than 64.5% of the US adult population were overweight or obese and across the US, 30.5% of the population were obese (Flegal et al., *JAMA* 288: 1723-1727 (2002)). There also appears to be a US epidemic in diabetes with 7.3% of the US population being diabetic (Mokdad et al., JAMA 286: 1195-1200 (2001)). While physicians advise their patients battling with weight gain, obesity and diabetes to exercise and manage the quantity as well as the quality of food eaten, the evidence suggests that a major portion of the population are unable or unwilling to make the major changes in lifestyle that may be necessary to decrease their body mass.

The strategies recommended by health care providers to reduce and/or maintain weight often involve changes in life style and in some cases the additional use of drugs or dietary supplements. Those individuals that are able to maintain weight loss (defined as >10% below the initial body weight after one year) generally adopt all or at least some combination of these strategies (McGuire et al., "Behavioral strategies of individual who have maintained long-term weight losses" *Obes Res* 7:334-341 (1999)). Nonetheless, despite all of the efforts made by obese individuals and governments, the success rate for keeping weight off is disappointingly low. A meta-analysis has shown that the success rate of "self-cure" ranged from 9% to 43% after a one-year follow-up (Bartlett et al., "Is the prevalence of successful weight loss and maintenance higher in the general community than the research clinic?" *Obes Res* 7:407-413 (1999)). The National Weight Control Registry has reported that 47%-49% of the obese patients maintained at least 10% weight loss after one year and 25% -27% have maintained this amount of weight loss over 5 years (McGuire et al., "The prevalence of weight loss maintenance among American adults" *Int J Obes Metab Disord* 23:1314-1319 (1999)). However, after 5-15 years, only 5% of the obese patients were able to maintain the weight loss (Drenick and Johnson, "Weight reduction by fasting and semistarvation in morbid obesity: long term follow-up". *Int. J Obes.* 2:25-34 (1978) and Sarlio-Lahteenkorva and Rissanen "A descriptive study of weight loss maintenance: 6 and 15 years follow-up of initially overweight adults" *Int J Obes* 24:116-125 (2000)).

Pharmaceutical treatments for obesity have been developed but their use has limitations. Currently there are only two Food and Drug Administration (FDA) approved antiobesity drugs, Orlistat and Sibutramine. Orlistat inhibits pancreatic lipase activity in the small intestine. Pancreatic lipase breaks down triglycerides into fatty acids and monoglycerides which are subsequently absorbed into the body. Thus inhibition of lipase activity effectively reduces fat absorption. However, if the patient fails to follow a reduced fat diet, which is recommended while on this medication, the fat is metabolized by the intestinal bacteria and causes osmotic shifts and gas production resulting in diarrhea and flatulence, rather unpleasant side effects of this medication. Thus, while this drug can induce modest weight loss and better weight maintenance than diet alone, in the absence of major dietary changes the adverse effects of gastrointestinal discomfort, diarrhea and flatulence have limited its use (Heck et al., "Orlistat, a new lipase inhibitor for the management of obesity". *Pharmacotherapy* 20:270-279(2000)).

Sibutramine is a serotonin and norepinephrine reuptake inhibitor and reduces body weight by suppressing appetite (Bray G., "Drug treatment of obesity". *Rev Endocr Metab Disord* 2:403-418(2001)). FDA has approved it for the treatment of obesity for up to 2 years. However, Sibutramine inhibits the reuptake of norepinephrine and thus may increase blood pressure. Therefore this drug is contraindicated for use in some obese patients (Bray 2001 supra and Sramek et al. "Efficacy and safety of sibutramine for weight loss in obese patients with hypertension well controlled by beta-adrenergic blocking agents: a placebo-controlled, double-blind, randomized trial" *J Hum Hypertens* 16:13-19 (2002)). Other side effects of Sibutramine include increased heart rate, insomnia, constipation, headache, abdominal pain etc. For normotensive obese patients, Sibutramine in combination of diet and behavioral modifications has shown beneficial effects (Astrup and Toubro "When, for whom and how to use sibutramine?" *Int J Obes Relat Metab Disord* 25 (suppl 4):S2-S7 (2001)) but to date there have been no human studies that used Sibutramine alone, that is without any life-style modifications. In addition, in one animal study, the appetite suppressing effects of Sibutramine gradually attenuated over several days of administration (Strack et al. "Regulation of body weight and carcass composition by sibutramine in rats" *Obes Res* 10:173-181 (2002)).

Dietary supplements have also been used to reduce weight gain, to maintain weight and to treat some of the metabolic abnormalities associated with obesity. For example, omega 3-fatty acids and linolenic acid have been shown to reduce weight gain and affect triglyceride levels and/or insulin resistance. Omega 3 fatty acids are known to reduce blood lipid levels in normal, hyperlipidemic and diabetic humans and have been reported to decrease body weight. Diabetic patients without hyperlipidemia fed a diet comprising fish oil, which is known to be high in omega 3 fatty acid, did not display reduced blood lipid levels, although their blood pressures were reduced. However, diabetic patients having hyperlipidemia had significantly reduced blood triglyceride levels and reduced blood pressure after the omega 3 fatty acid fish oil feeding (Kasmin et al. *J. Clin Endocrinol Metab* 67:1-5 (1988)). The effect of diets comprising fish oil fed to genetically obese Zucker rats and their lean counterparts demonstrated that both the obese and normal rats had a reduction in body weight and blood lipid levels as compared to controls (Jen et al., *Nutrition Research* 9:1217-1228 (1989)). A high fat diet made with fish oil induced the least amount of weight gain and insulin resistance compared to a high fat diet made with other types of oil(Pellizzon et al., Obesity Res. 10:947-955 (2002)) Omega 3 fatty acids also appear to beneficially affect insulin resistance. Rats fed high fat diets comprising fish oil had less insulin resistance than rats fed diets comprising other oils, e.g., lard, corn oil or medium chain triglycerides (Hill et al. *Int. J. Obesity*, 17:223-236 (1993)).

Linolenic acid added to diets has also been shown to reduce body fat content and to facilitate fatty acid β-oxidation in the liver (Takada et al., *J. Nutr.* 124:469-474 (1994)). Aged rats were fed diets made with various fatty acids, i.e., α-linolenic acid (n-3 PUFA) or gamma linolenic acid (n-6 PUFA) (10% w/w) with added cholesterol for 15 weeks and it was found that both the α-and gamma linolenic diets inhibited the increase in blood total cholesterol, VLDL+IDL+LDL cholesterol levels in the rats when fed high cholesterol diets (Fukushima et al. *Lipids* 36:261-266 (2001)). Similar results were found in obese Zucker rats which had reduced body weight gain and body fat when gavaged daily with gamma linolenic acid (Phinney et al. *Metabolism* 42:1127-1140 (1993)). In humans, a mixture of n-3 PUFA and gamma linolenic acid also favorably altered blood lipids and fatty acid profiles in women after administration for about 28 days (Laidlaw and Holub, *Am J. Clin. Nutr.* 77:37-42 (2003)).

Life style changes to promote weight loss and other beneficial health effects include e.g. an increase in physical activity; a reduced caloric intake and a reduced dietary fat intake. The United States has seen a gradual reduction in the percentage of dietary fat intake from 43.7% in 1965 to 33.1% in 1995 (Kennedy et al., "Dietary-fat intake in the US populatio" *J Am Coll Nutr* 18:207-212 (1999)), however, the average number of calories eaten has increased more than the increase in fat consumption. Therefore even though the percentage of dietary fat intake has decreased, the total fat intake has increased since 1995 to 100.6 g (males). Due to the relative ease with which dietary fat is converted to adipose tissue, a diet high in fat leads to an elevated weight gain as compared to a lower fat diet even though the calorie intake is comparable. This phenomenon has been reported to occur in both humans and rats (Astrup et al., "Obesity as an adaptation to a high-fat diet: evidence from a cross-sectional study" *Am J Clin Nutr;* 59:350-355 (1994)); (Jen "Effects of diet composition on food intake and carcass composition in rats" *Physiol Behav* 42:551-556 (1988) and; Jen et al., "Long-term weight cycling reduces body weight and fat free mass, but not fat mass in female Wistar rats" *Int J Obesity* 19:699-708 (1995)).

Various low fat and/or low calorie foods have been developed in an effort to promote weight loss or inhibit weight gain. Many "low fat" foods are prepared by reducing the percentage of fat but the percentage of carbohydrates in the foods is increased to make the foods more palatable by compensating for the loss of the taste and texture provided by the fat. Increasing the amount of carbohydrates, e.g., sugars, in the food often make the foods "low fat" but the caloric content may not be reduced and in many instances is actually increased. Many low calorie food are prepared by simply replacing the caloric components of the food with a non-caloric filler, e.g., a dietary fiber. However, replacing significant portions of carbohydrates with fiber fillers often alters the taste and texture of the food making the food less palatable for some consumers. In addition, consumption of large amounts of dietary fiber often have unwanted side effects such as e.g., flatulence, and a diet comprising more than about 60 g fiber may result in deficiencies in calcium, iron, zinc and increased risk of bowel obstruction. While high fiber diets, comprising about 25-35 g/d are recognized as having beneficial effects, e.g., reducing blood triglycerides and cholesterol levels, many persons should not take high levels of fiber, e.g., the elderly, growing children and those suffering from particular medical conditions e.g., acute or subacute diverticulitis, and the acute phases of certain inflammatory conditions of the bowel, e.g., ulcerative colitis or Crohn's disease. After some types of intestinal surgery, e.g., a colostomy or ileostomy, a low fiber, low residue diet is used as a transition to a regular diet is preferred. Thus it is desirable to develop a food product that has the taste and texture desired by consumers but also reduces weight gain, blood triglycerides and cholesterol levels and is not necessarily high fiber.

Cyclodextrins are a family of cyclic polymers of glucose produced by enzymatic digestion of cornstarch with a cyclodextrin glyceryltransferase. α-, β- and γ-cyclodextrins contain 6, 7 and 8 glucose molecules and take on a toroid or truncated cone conformation in aqueous solution. The molecules have a hydrophobic interior and hydrophilic exterior forming an internal pore. The different polymer lengths yield different pore sizes.

The unique properties of β and γ-cyclodextrins have been exploited in a variety of fields. For example, they have been used to stabilize and solubilize drugs and also to enhance food flavors. While the β and γ-cyclodextrins have found considerable use in the pharmaceutical and food industries., α-cyclodextrin has found relatively little use in these industries because of its small pore size as well as the fact that it does not appear to be metabolized by pancreatic amylase or intestinal flora (Suzuki and Sato, "Nutritional significance of cyclodextrins: indigestibility and hypolipemic effect of α-cyclodextrin" *J Nutr Sci Vitaminol (Tokyo)* 1985; 31:209-223), although this latter aspect has been disputed by one of the manufacturers of the material (Antlsperger G S G. "Toxicological comparison of cyclodextrins" presented in the 8th International Cyclodextrin Symposium in Budapest 1996:1-7). α-cyclodextrin efficiently complexes free fatty acids (FFA) in solution (McGowan et al. "A peroxidase-coupled method for the colorimetric determination of serum triglycerides" *Clin. Chem.* 29(3):538-542 (1983)) and has been used to eliminate the turbidity caused by FFA in a number of clinical diagnostic reagents (Morgan, Artiss and Zak "A study of turbidity in hypertriglyceridemic specimens" *Microchem. J.* 64:147-154(2000)). α-cyclodextrin has also been used for the specific and selective removal of free fatty acids from used cooking oil (U.S. Pat. No. 5,560,950).

Previous studies disclose that α-cyclodextrin is essentially indigestible and may exert an effect on weight gain only if it exceeds about 20% of the total dietary intake, as determined in a rat model. Japanese patent application JP 05-298849 (Publ. No. 07115934) assays the effects of linolenic acid and α-cyclodextrin on weight gain in rats. This application reports that rats fed diets comprising either 16% α-cyclodextrin or 1% linolenic acid gain weight approximately the same as rats fed a control diet. In contrast, this Japanese application discloses that rats fed diets comprising a combination of 14% α-cyclodextrin and 2% linolenic acid incur significant weight loss. Japanese patent application S60-149752 also analyzes the effect of linolenic acid in combination with α-cyclodextrin on weight gain in rats. This application reports that a diet comprising 14% w/w α-cyclodextrin has little effect on weight gain in rats while the combination of 14% w/w α-cyclodextrin and 0.5% w/w linolenic acid produces significant weight loss. Japanese patent application H5-298850 analyzes the effects of diets comprising linolenic acid (1.5-2% w/w) and α-cyclodextrin (14% w/w) and a barley green element. This application reports that the diets comprising 14% w/w α-cyclodextrin in combination with 1.5-2% w/w linolenic acid produce only a small decrease in body weight while the addition of a barley green element to the linolenic acid and cyclodextrin results in significant reduction in weight gain. This application does not report the effects of diets comprising only α-cyclodextrin as the additional component. None of these applications discloses the fat content of the diets and they teach the importance of additional ingredients and/or the ineffectiveness of α-cyclodextrin alone.

Japanese patent application H4-333575 supplemented the diet of rats with particular total amounts of linolenic acid and/or α-cyclodextrin and/or a peptide hydolysate by gavaging rats with wheat starch compositions comprising either 0.9% w/w linolenic acid alone, 9% w/w α-cyclodextrin alone, or 100% w/w of a compositions of small molecular weight hydrolytes of a larger molecular weight protein, or with compositions comprising combinations of the three components. The fat content of the diets was not described. Only the diets containing a combination of linolenic acid, α-cyclodextrin and the peptide hydrolysate displayed a significant change in the rate of weight gain over time.

Japanese applications JP05-113603 (Publ. No. 08187060) and JP05-164024 (Publ. No. 06343419) assay the effect of a mixture of about 15% α-cyclodextrin and 1.5% linolenic acid on weight gain in humans. The applications disclose that subjects ingesting the α-cyclodextrin/linolenic acid compositions in an amount based on their body weight, such that the daily dose of the composition was about 0.015 g/kg body weight three times a day, which is 1.37 g/91 kg (2001b) individual three times per day, which corresponds to 4.11 g of total composition per day or 0.62 g α-cyclodextrin per day (0.21 g/meal) and 0.068 g linolenic acid per day (0.023 g/meal), display a significant increase in weight loss as compared to subjects who did not ingest the combination. However, these applications did not assay the effect of α-cyclodextrin alone or linolenic acid alone nor did they disclose the fat content of the diets. Linolenic acid is well known to reduce weight and fat gain in both animal and human studies (Jen et al., *Nutri. Res* 9:1217-1228 (1989) and Takada et al., *J. Nutri.* 124:469-474 (1994) and Couet et al. *Int. J. Obes.* 21:637-643 (1997)) and is likely to be the component that actually promoted the observed weight loss reported in these applications.

U.S. Pat. No. 4,880,573 discloses a process for eliminating cholesterol from fatty substances of animal origin, e.g. lard, suet or butter. The process combines β-cyclodextrin with the liquified fatty substance under a non-oxidizing atmosphere and then removes the complexes of cholesterol and cyclodextrin leaving a fatty substance free of cyclodextrin and with a reduced cholesterol content.

U.S. Pat. No. 5,189,149 discloses the use of complexes of cyclodextrins and long chain fatty acids, their salts and esters, inclusive of fish and vegetable oil glycerides, to deliver long chain fatty acids to a subject and avoid the unctuous characteristics associated with the fish and vegetable oil glycerides and their unpleasant taste and odor.

U.S. Pat. No. 5,232,725 relates to a process for reducing the cholesterol and free fatty acids in a fat containing material, e.g., fresh cream, by combining water, the fat containing material and cyclodextrin under conditions suitable for forming an oil-in-water type "fine" emulsion, which facilitates the formation of complexes of cyclodextrin and cholesterol or free fatty acids. The complexes are then mechanically separated to produce a fat-containing material with reduced levels of cholesterol and free fatty acids. U.S. Pat. No. 5,232,725 does not describe a food product comprising complexes of triglyceride and α-cyclodextrin, wherein the bioavailability of the fat in the food product is reduced, as described herein.

U.S. Pat. No. 5,560,950 relates to a process for reducing the free fatty acid content of a used oil by mixing the used oil with cyclodextrin, preferably with an absorbent, e.g., silica, under conditions that form agglomerates of cyclodextrin/absorbent and fatty acids and then removing the cyclodextrin agglomerates from the oil. The process produces a oil that is cyclodextrin free and has a reduced level of free fatty acids.

U.S. Pat. No. 5,571,554 relates to a process for reducing triglycerides in an egg yolk by preparing a mixture of egg yolk with water, or a salt solution, and combining the mixture with a cyclodextrin and then removing the cyclodextrin and the added water or salt solution. The process produces a cyclodextrin free egg yolk product with reduced levels of triglycerides.

U.S. Pat. No. 5,738,898 relates to a process for reducing cholesterol in egg yolk by preparing a mixture of egg yolk, water and cyclodextrin at a pH between 7.5 and 12. The cyclodextrin cholesterol complexes are removed and the pH adjusted to pH 6-7. The process produces a cyclodextrin free egg yolk product with reduced cholesterol.

Many consumers, including obese individuals, appear to have a preference for foods that have a high fat content (Mela and Sacchetti, "Sensory preferences for fats: relationships with diet and body composition" *Am J Clin Nutr* 1991;53: 908-915). Thus, it is very difficult for many individuals, particularly obese individuals, to reduce their fat intake in order to reduce their body weight and the adverse health effects associated with increased weight gain. Therefore, a substance that reduces the absorption of dietary fat without the unpleasant side effects of the current medications is extremely desirable. Such a substance would have significant health benefits in reducing obesity and its related disorders, such as Type II diabetes (NIDDM). It would be desireable to develop a food product that promotes weight loss, reduces lipid levels and reduces the symptoms of other disorders associated with weight gain/obesity and yet has desirable organoleptic properties. Described herein are fat containing consumable products having the organoleptic properties such as taste, texture and moistness that consumers desire and yet promote weight loss and other health benefits.

SUMMARY OF THE INVENTION

This invention relates to a fat containing consumable food product that comprises α-cyclodextrin and fat wherein the ratio of α-cyclodextrin to fat is about 1:20 w/w -1:3 w/w. Preferably the ratio of α-cyclodextrin to fat is about 1:13 w/w -1:5 w/w, and most preferably the ratio of α-cyclodextrin to fat is about 1:9 w/w. The total cyclodextrin in the foods of this invention is less than about 9-10% w/w, preferably less than about 6%, and more preferably below 3% w/w, and particularly in the case of fat containing consumable farinaceous food products of this invention the amount of total cyclodextrin is below about 3% w/w. Preferably the fat containing food products of this invention comprise, by caloric content, about 7% to about 80% fat, preferably about 20% to about 70% fat, more preferably about 40% to about 70% fat, or by weight, 5% to about 50% w/w fat, preferably about 5-30% w/w fat, and more preferably about 7-25% w/w fat. "Fats" as defined herein are triglycerides. Cyclodextrins are often sold as mixtures of α, β-, γ-cyclodextrin and n-dextrin. Preferably the α-cyclodextrin composition that may be used in the products and methods of this invention, is a substantially pure α-cyclodextrin comprising at least about 95% α-cyclodextrin, preferably at least 98% α-cyclodextrin. The α-cyclodextrin in the foods herein may provide a source of fiber in addition to its other beneficial effects. The consumable products may be a farinaceous food product or a non-farinaceous food product, e.g., a dairy food product, a prepared vegetable product, or a prepared meat product, e.g. a prepared beef, lamb, pork, poultry or seafood food product. The consumable food products of this invention are suitable for consumption by mammals, e.g., mice, rats, cats, dogs and humans but preferably humans.

Cyclodextrins have been used previously in methods to reduce the levels of free fatty acids, cholesterol or triglycerides in food products but in contrast to the food products of this invention, those methods produced products that are essentially cyclodextrin free and have reduced levels of free fatty acids, cholesterol and triglycerides as compared to a like food product that has not been treated. If assayed by bomb calorimetry, the products produced by those methods will have a lower caloric content due to the reduced levels of cholesterol and triglycerides. The consumable food products of this invention comprise α-cyclodextrin and do not have reduced levels of fatty acids, cholesterol or triglycerides as compared to a like food product without the added α-cyclodextrin. As such, the consumable products of this invention do not have a substantially reduced caloric content, as assayed by bomb calorimetry, as compared to a like product that does not contain α-cyclodextrin, and yet the food products of this invention inhibit the rate of weight gain, promote weight loss and provide other health benefits. Thus the consumable food product of this invention is a diet food that inhibits the rate of weight gain, promotes weight loss and provides other health benefits.

Shimada et al. (Shimada et al. "Structure of inclusion complexes of cyclodextrins with triglyceride at vegetable oil/water interface" *J. Food Sci.* 1992; 57(3):655-656) reported that two molecules of α-cyclodextrin complex with one fatty acid group (FFA), while Szejtli (Szejtli J. "Utilization of cyclodextrins in industrial products and processes" *J. Mater. Chem.* 1997;7:575-587) suggests that this phenomenon is dependent upon the chain length of the fatty acids and that it is possible for 3-4 molecules of α-cyclodextrin to complex with each of the three fatty acids of a triglyceride molecule, which suggests 9-12 molecules of α-cyclodextrin would be required to completely complex one molecule of triglyceride. If this were the case it would be difficult to imagine being able to feed enough α-cyclodextrin to an animal to complex sufficient amounts of triglycerides to make a significant difference in body weight.

Suzuki et al. infra and Kaewprasert et al. infra both report that a cyclodextrin composition alone mixed into a food does not promote significant weight loss, even at concentrations of 20% w/w of total dietary intake. In particular, Suzuki et al., *Denpun Kagaku* 30(2):240-246 (1983) analyzed the effect of a diet comprising 20% cyclodextrin on the weight gain of rats and reported that there were no differences in the weight gain of rats fed a 20% cyclodextrin diet and those fed a 20% starch diet. Likewise, Kaewprasert et al., *J. Nutri. Sci. Vitaminol.* 47:335-339 (2001) reported that the body weight gain in rats fed a 5% α-cyclodextrin diet was not significantly different from rats fed control diets. Kaewprasert discloses a diet comprising cyclodextrin and fat at a ratio of about 1:1.4. Suzuki did not discuss the fat content of the experimental diets or disclose the ratio of cyclodextrin to fat in the diet. This effect of relatively large amounts of cyclodextrin was also noted in Japanese application S60-094912. S60-094912 suggests that cyclodextrins may inhibit the rate of weight gain and decrease neutral fat (triacylglycerides) in liver and plasma, but only if cylodextrin is administered at levels of 20% w/w and more. Likewise Suzuki and Sato, *J. Nutri. Sci. Vitaminol.* 31:209-223 (1985) report that rats fed diets comprising a mixture of n-dextrin and α-, β- and γ-cyclodextrins (50:30:15:5% w/w) displayed a weight loss substantially different from the control group only when at least 58.5% w/w of the diet consisted of the cyclodextrin mixture. In contrast, we have found that significant weight loss can be obtained in subjects with much lower levels of α-cyclodextrin if the subjects are consuming fat containing diets and the ratio of ingested α-cyclodextrin to ingested fat in the diet is sufficient to form complexes of fat and cyclodextrin. The body naturally forms a fine emulsion of fat in water, which is necessary for lipase to catalyze the hydrolysis of fat. Without wishing to be bound by theory, the invention described herein disrupts this process by forming large complexes of α-cyclodextrin and fat so that the lipase cannot act on the fat. Thus the fat in the fat containing food products of this invention is not bioavailable because it is in the form of α-cyclodextrin/fat complexes that are resistant to lipase activity.

The levels of cyclodextrin in the foods of this invention are well below the levels that S60-94912 and Suzuki and Sato (*J Nutri Sci Vitaininol* 1985 supra) indicate are necessary for weight loss. The total cyclodextrin in the foods of this invention is less than about 9% w/w, preferably less than about 6% w/w, and more preferably below 3% w/w, particularly in the case of the consumable farinaceous food products of this invention. Subjects fed a diet comprising the α-cyclodextrin-containing foods of this invention, preferably those which comprise the amounts of α-cyclodextrin disclosed herein and wherein the α-cyclodextrin to fat ratio is within the ratios disclosed herein, display inter alia weight loss, increase in HDL levels and a reduction in blood triglycerides.

Without wishing to be bound by theory, the results presented herein suggest that the α-cyclodextrin is particularly suitable for complexing fat in a food composition thereby reducing the fat's bioavailability. By ingesting α-cyclodextrin in an appropriate amount with a fat-containing meal, or shortly before or after ingesting a fat-containing meal, a subject may complex the ingested fat and inhibit its absorption by the body. The amount of α-cyclodextrin should be sufficient to form complexes with the fat thereby reducing the fat bioavaibility, preferably the amount of α-cyclodextrin is sufficient to obtain a ratio of α-cyclodextrin to fat of 1:20 to 1:3, preferably 1:13 to 1:5 and more preferably about 1:9 such that complexes of fat and cyclodextrin are formed. Without wishing to be bound by theory, it is the reduction in the bioavailability of the ingested fat (the amount of ingested fat that is absorbed and thus available to the body for use) that results in, e.g., the observed weight loss, increase in HDL cholesterol, decreased leptin levels and reduction in serum triglycerides.

This invention also relates to methods for complexing fat contained in an ingested food product, particularly a high fat food product, thus reducing the bioavailability of the ingested fat. The method comprises ingesting an amount of an α-cyclodextrin with a food product such that the ratio of α-cyclodextrin to fat of about 1:20 to about 1:3 w/w preferably about 1:13 to about 1:5 w/w most preferably about 1:9 w/w. The α-cyclodextrin may be ingested prior to, concurrently with or subsequent to ingestion of the food product. At such ratios the fat is complexed with the α-cyclodextrin and the bioavailability of the ingested fat is reduced. Alternatively the α-cyclodextrin my be combined with the food product prior to consumption in an amount such the ratio of α-cyclodextrin to fat in the ingested food product is about 1:20 to about 1:3 w/w preferably about 1:13 to about 1:5 w/w most preferably about 1:9 w/w and the food product comprising the α-cyclodextrin and fat is ingested.

This invention also relates to methods for producing a fat containing food product having fat with reduced bioavailability by forming complexes of α-cyclodextrin and fat within the food product, particularly a high fat food product. The method comprises combining α-cyclodextrin with a food product under conditions that favor the formation of complexes of fat and α-cyclodextrin, wherein the conditions avoid the formation of a fine emulsion of fat within the food product. The amount of an α-cyclodextrin is such that the food product comprises a ratio of α-cyclodextrin to fat of about 1:20 to about 1:3 w/w preferably about 1:13 to about 1:5 w/w most preferably about 1:9 w/w. At such ratios and under such conditions, the fat is complexed with the α-cyclodextrin the bioavailability of the ingested fat is reduced. The food product may be a farinaceous food product e.g., snack bars, breakfast cereals, pancakes, waffles, muffins, fruit filled pastries, tortillas, corn chips, tortilla chips, snack crackers, breads, cakes, cookies, or pies, or non-farinaceous food product, e.g, a vegetable, dairy, or meat food product e.g. french fries, tempura, veggie burgers, refried beans, hummus, tahini, margarine and nut butters, (e.g., peanut, cashew, almond, hazelnut), marzipan, potato chips; milk, cream, pudding, butter, ice cream, and cheese and processed cheese products, prepared beef, lamb, pork, poultry or seafood products, e.g., frankfurters, deli slices, sausages, fish sticks, chicken fingers, and ground meats, e.g., meatloaf, meatballs and hamburgers, yogurt and yogurt products, and egg products.

Thus this invention also relates to a method for promoting weight loss or inhibiting weight gain in a subject comprising administering to a subject in need thereof α-cyclodextrin in an amount and for a time sufficient to produce a weight loss or inhibit weight gain. Preferably the α-cyclodextrin is administered to a subject consuming an average fat diet (about 100 g fat/day, about 33 g fat/meal) wherein the amount administered to the subject is such that the ratio of α-cyclodextrin to fat ingested per meal, or daily, by the subject is about 1:20 to about 1:3 w/w, preferably the ratio is about 1:13 to about 1:5 w/w and more preferably about 1:9 w/w. Once the desired weight is lost, the α-cyclodextrin may be included in the diet in an amount to inhibit or preferably prevent weight gain. For a loss of about 1-1.5 lbs per week for a subject whose dietary intake is 100 g fat/day (about 33 g fat/meal), the amount of α-cyclodextrin administered is preferably about 2 g/meal, thus reducing the bioavailability of approximately 54 g of fat per day.

Serum cholesterol is found in combination with proteins in the blood. Of particular interest are high density (HDL the good cholesterol) and low density lipoprotein (LDLs the bad cholesterol). This invention relates to a method for increasing the level of high density lipoprotein (HDL) in a subject comprising administering α-cyclodextrin to a subject in need thereof in an amount and for a time sufficient to increase HDL levels. Preferably the amount α-cyclodextrin administered to the subject is about four to about eleven grams per day. Preferably, the α-cyclodextrin is administered in an amount such that the ratio of α-cyclodextrin to fat ingested per meal, or daily, is about 1:20 to 1:3 w/w more preferably 1:13-1:5 w/w or most preferably about 1:9w/w. The α-cyclodextrin may be administered in a variety of forms, e.g., a tablet, capsule, pill, elixir, wafer, beverage, or in a food product, e.g., bread products, e.g., buns, rolls, biscuits, and breakfast cereals, e.g., oatmeal, cream of wheat, raisin bran, corn flakes, or other ready to eat cereals, meat products and dairy products, and particularly the consumable food products of this invention. Preferably the tablet, pill, capsule, elixir, wafer, beverage, or the consumable food products comprises a cyclodextrin that is predominantly α-cyclodextrin, e.g., the cyclodextrin is at least about 90-98% α-cyclodextrin.

It is possible that the total levels of cholesterol in the blood will remain constant even though the levels of HDL are elevated if there is a reduction in the levels of LDL. Preferably the total cholesterol levels are substantially reduced or are unchanged by the methods of this invention. Thus, this invention also relates to a method for reducing the cholesterol/HDL ratio in a subject comprising administering to a subject in need thereof α-cyclodextrin in an amount and for a time sufficient to reduce the cholesterol/HDL ratio. The α-cyclodextrin may be administered in a variety of forms, e.g., a tablet, pill, capsule, elixir, wafer, beverage, or in food products, e.g., bread products, e.g., buns, rolls, biscuits, and breakfast cereal, e.g., oatmeal, cream of wheat, raisin bran, corn flakes, or other ready to eat cereal, and particularly the consumable food products of this invention. The tablet, pill, capsule, elixir, wafer, beverage, or food products may contain α-cyclodextrin in combination with other cyclodextrins, e.g. β and/or γ cyclodextrins or with n-dextrin. Preferably the cyclodextrin in the tablet, pill, capsule, elixir, wafer, beverage, or the food products is predominantly α-cyclodextrin, e.g., the cyclodextrin is at least about 90-98% α-cyclodextrin.

This invention also relates to a method of reducing triglyceride levels in a subject comprising administering to a subject in need thereof an amount of α-cyclodextrin sufficient to reduce triglyceride levels. The amount of α-cyclodextrin administered to the subject is such that the ratio of α-cyclodextrin to fat ingested per meal, or daily, by the subject is about 1:20 to about 1:3 w/w, preferably the ratio is about 1:13 to about 1:5 w/w and more preferably the ratio is about 1:9 w/w. The α-cyclodextrin may be administered in a variety of forms, e.g., a tablet, capsule, pill, elixir, wafer, beverage, or in food products, e.g., bread products, e.g., buns, rolls, biscuits, and breakfast cereal, e.g., oatmeal, cream of wheat, raisin bran, corn flakes, or other ready to eat cereals, and, particularly the consumable food products of this invention. The tablet, pill, capsule, elixir, wafer, beverage, or food products may contain α-cyclodextrin in combination with other cyclodextrins, e.g. β and/or γ cyclodextrins or with n-dextrin, but preferably the cyclodextrin in the tablet, pill, capsule, elixir, wafer, beverage or the food products is predominantly α-cyclodextrin, e.g., the cyclodextrin is at least about 90-98% α-cyclodextrin.

This invention further relates to a method for reducing leptin levels in a subject comprising administering α-cyclodextrin to a subject in need thereof in an amount and for a time sufficient to reduce leptin levels in the subject. The α-cyclodextrin may be administered in a variety of forms, e.g., a tablet, capsule, pill, elixir, wafer, beverage or in food products, e.g., bread products, buns, rolls, biscuits and breakfast cereal, e.g., oatmeal, cream of wheat, raisin bran, corn flakes, or other ready to eat cereals, and particularly the consumable food products of this invention. The tablet, pill, capsule, elixir, wafer, beverage or food products may contain α-cyclodextrin in combination with other cyclodextrins, e.g. β and/or γ cyclodextrins or with n-dextrin, but preferably the cyclodextrin in the tablet, pill, capsule, elixir, wafer, beverage or the food products is predominantly α-cyclodextrin, e.g., the cyclodextrin is at least about 90-98% α-cyclodextrin.

This invention also relates to a method for suppressing appetite by administering α-cyclodextrin to a subject in need thereof in an amount and for a time sufficient to suppress the subject's appetite. The amount of α-cyclodextrin administered to the subject is such that the ratio of α-cyclodextrin to fat ingested per meal, or daily, by the subject is about 1:20 to about 1:3 w/w, preferably the ratio is about 1:13 to about 1:5 w/w and more preferably the ratio is about 1:9 w/w. The α-cyclodextrin may be administered in a variety of forms, e.g., a tablet, capsule, pill, elixir, wafer, beverage or in food products, e.g., bread products, buns, rolls, biscuits, and breakfast cereal, e.g., oatmeal, cream of wheat, raisin bran, corn flakes, or other ready to eat cereals, and particularly the consumable food products of this invention. The tablet, pill, capsule, elixir, wafer, beverage or food products may contain α-cyclodextrin in combination with other cyclodextrins, e.g. β and/or γ cyclodextrins or with n-dextrin, preferably the cyclodextrin in the tablet, pill, capsule, elixir, wafer, beverage or the food products is predominantly α-cyclodextrin, e.g., the cyclodextrin is at least about 90-98% α-cyclodextrin.

This invention further relates to a method for reducing insulin levels and insulin resistance in a subject comprising administering α-cyclodextrin to a subject in need thereof in an amount and for a time sufficient to reduce insulin levels and insulin resistance in the subject. Preferably the amount of α-cyclodextrin administered to the subject is such that the ratio of α-cyclodextrin to fat ingested per meal or daily by the subject is in a ratio of about 1:20 to about 1:3 w/w, preferably the ratio is about 1:13 to about 1:5 w/w and more preferably the ratio is about 1:9 w/w. The α-cyclodextrin may be administered in a variety of forms, e.g., a tablet, capsule, pill, elixir, wafer, beverage or in food products, e.g., bread products, buns, rolls, biscuits, and breakfast cereal, e.g., oatmeal, cream of wheat, raisin bran, corn flakes, or other ready to eat cereal, and particularly the consumable food products of this invention. Preferably the cyclodextrin in the tablet, pill, capsule, elixir, wafer, beverage or food products is predominantly α-cyclodextrin, e.g., the cyclodextrin is at least about 90-98% α-cyclodextrin.

This invention also relates to a method for reducing diarrhea in a subject in need thereof comprising administering to a subject in need thereof α-cyclodextrin in an amount and for a time sufficient to reduce diarrhea in the subject. Preferably the amount of α-cyclodextrin administered to the subject is such that the ratio of α-cyclodextrin to fat ingested per meal or daily by the subject is in a ratio of about 1:20 to about 1:3 w/w, preferably the ratio is about 1:13 to about 1:5 w/w and more preferably the ratio is about 1:9 w/w. The α-cyclodextrin may be administered in a variety of forms, e.g., a tablet, capsule, pill, elixir, wafer, beverage or in food products, e.g., bread products, buns, rolls, biscuits, and breakfast cereal, e.g., oatmeal, cream of wheat, raisin bran, corn flakes, or other ready to eat cereals, and particularly the consumable food products of this invention. Preferably the cyclodextrin in the tablet, pill, capsule, elixir, wafer, beverage or the food products is predominantly α-cyclodextrin, e.g., the cyclodextrin is at least about 90-98% α-cyclodextrin.

This invention also relates to methods for enhancing organoleptic properties of a fat containing food product without reducing the percentage of fat in the food product or the caloric content due to the fat, as assayed by bomb calorimetry. The method comprises adding α-cyclodextrin to the fat containing food product such that it is present during processing and in the final ingested food product. The amount of α-cyclodextrin that is added to the food product may be based on the amount of fat in the finished consumable product.

DESCRIPTION OF THE INVENTION

Figure 1:
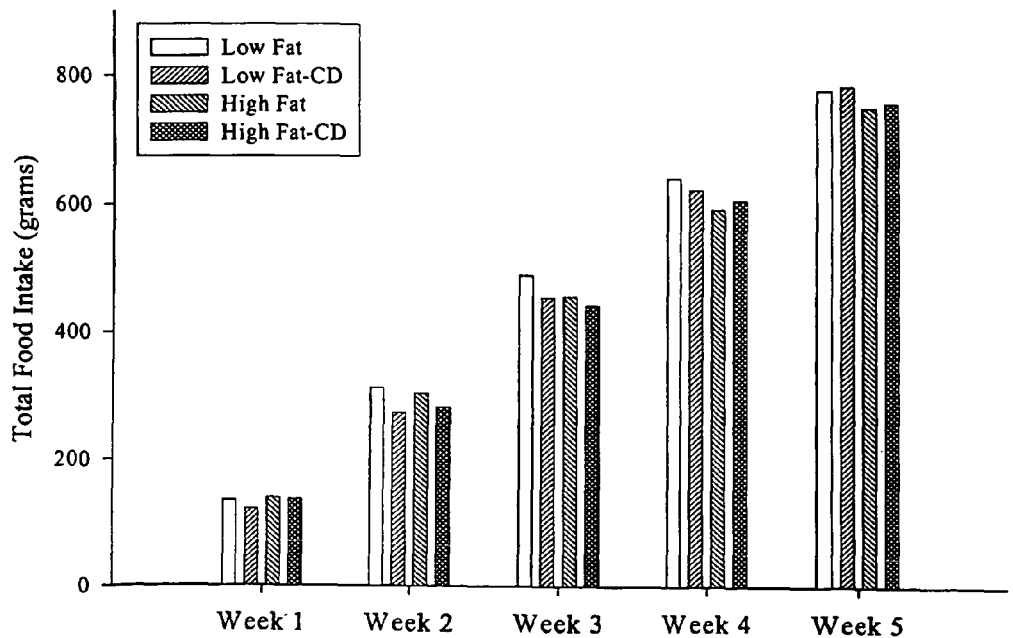
FIG. 1 depicts the cumulative total mass of food consumed by the four groups of rats and demonstrates that there was no significant difference in the mass of food consumed by the different groups.

This invention relates to a fat containing consumable food product containing α-cyclodextrin and to methods for its use. The consumable food products are suitable for consumption by mammals, e.g., a mouse, rat, a cat, a dog, a cow, a horse, a monkey, an ape or a human, and thus include e.g., a pet food product for a e.g. cat, dog or horse or a human consumable food product. The consumable food products of this invention comprise α-cyclodextrin and fat, preferably the ratio of the amount of α-cyclodextrin to fat is about 1:20-1:3 w/w, more preferably the ratio of α-cyclodextrin to fat of about 1:13-1:5 w/w, and most preferably the ratio of α-cyclodextrin to fat of about 1:9 w/w. Preferably the total cyclodextrin in the consumable food products is less than about 9% w/w, more preferably the total cyclodextrin in the consumable food products is less than about 6% w/w and most preferably the total cyclodextrin in the food products is less than about 3%. Preferably complexes of cyclodextrin and fat are distributed evenly throughout the food product. Preferably the consumable food products of this invention are high fat containing food products comprise by caloric content about 7% to about 80% fat, preferably about 20% to about 70% fat, more preferably about 40% to about 70% fat, or by weight about 5% w/w fat to about 50% w/w fat preferably about 5-30% w/w fat and more preferably about 7% w/w fat to about 25% fat. Methods for determining or calculating the amount of fat in a food product are well known in the art. See for example the software program "Food Processor" by ESHA Research, Salem, Oreg., incorporated herein by reference. Preferably the food products of this invention are made with less than 2% linolenic acid, more preferably less than 0.2% linolenic acid. More preferably the food products of this invention are made without detectable levels of linolenic acid. Linolenic acid has been shown to promote weight loss but at the levels necessary to promote weight loss, about 2%, the shelf life of products containing the linolenic acid are reduced due to its tendency to become rancid. In addition, high purity linolenic acid is very expensive. Thus linolenic acid is preferably not added to the food products of this invention before, during or after their preparation.

Various forms of cyclodextrins are commercially available. For example, Wacker-Chemie GmbH produces a variety of natural and modifed cyclodextrins. Cyclodextrins are often sold as mixtures of α-, β- and γ-cyclodextrins and can be produced by a variety of methods. Generally cyclodextrins are produced by treating a starch, e.g. potato or corn, with a cyclodextrin transferase, which is produced by a variety of organisms, e.g., *Bacillus macerans*. The cyclodextrins may be isolated from the treated starch using a variety of methods that combine concentration, fractionation, filtration, spray drying, granulation etc. For a more complete discussion of methods for the production and isolation of cyclodextrins see e.g. Schmid "Preparation and industrial production of cyclodextrins", *Comprehensive Supramolecular Chemistry* (1996), 3: 41-56. Eds Szejtli, Jozsef; Osa, Tetsuo. Elsevier, Oxford, UK incorporated herein by reference.

The fat containing consumable food products of this invention may be a farinaceous food product, e.g., snack bars, breakfast cereals, pancakes, waffles, muffins, fruit filled pastries, tortillas, corn chips, tortilla chips, snack crackers, breads, cakes, cookies, or pies, or a non-farinaceous food product, e.g. a prepared vegetable product (vegetables as described herein include vegetables, fruits and nuts), particularly those made with a fat ingredient, e.g. french fries, tempura, veggie burgers, refried beans, hummus, tahini, margarine and nut butters, (e.g., peanut, cashew, almond, hazelnut), marzipan, potato chips; a dairy food product e.g., milk, cream, pudding, butter, ice cream, and cheese and processed cheese products; yogurt and yogurt products, egg products and meat products, e.g., prepared beef, lamb, pork, poultry or seafood products, e.g., frankfurters, deli slices, sausages, fish sticks, chicken fingers, and ground meats, e.g., meatloaf, meatballs and hamburgers. Preferably the dairy product is one wherein α-cyclodextrin/fat complexes are distributed throughout the product, preferably a solid or semi-solid dairy product e.g., pudding, butter, ice cream, and cheese and processed cheese products and yogurt and preferably the organoleptic properties of the product are not adversely affected. The food products of this invention may also include among others, e.g., a pre-packaged farinaceous food product, e.g., a pre-packaged prepared pasta dish such as, e.g., lasagna, manicotti, spaghetti with sauce, ravioli, tortellini, or macaroni and cheese, or a packaged dairy product, a packaged prepared vegetable product, or a pre-packaged prepared meat product, wherein the food product comprises α-cyclodextrin and fat in ratios as set forth herein. Preferably, a serving of the pre-packaged product provides about 160 mg to 11 g α-cyclodextrin/serving, preferably about 1 g to about 7 g/serving and more preferably about 2-4 g per serving, and most preferably at about 2-3 g/serving. A pre-packaged food product may be enclosed in plastic, paper, cardboard or metal, e.g., tin or flexifoil. The pre-packaged food product may be packaged in bulk, multiserving packages or packaged as single servings.

This invention also relates to confectionery products e.g., hard candies such as lollipops and breath mints or after dinner mints, and condiments, e.g., gravies, sauces, salad dressings, mayonnaise etc., comprising α-cyclodextrin. Preferably, the confectionery product is a fat containing product such as, e.g., chocolates.

The α-cyclodextrin may be added to a consumable food product that is cooked, e.g., baked, roasted or fried, or to an uncooked consumable food product, e.g., milk, cream, whipped cream, non-dairy whipped toppings or fillings, yogurt or a beverage, e.g. a milkshake, eggnog, or a smoothie (fruit and yogurt drink). The α-cyclodextrin may be added to the food product at any stage of its preparation, e.g., the α-cyclodextrin may be mixed with the ingredients so that it is distributed throughout the food product and the product may then be cooked. However, in some instances the α-cyclodextrin may be applied to the surface of the food product, e.g., as a glaze or coating, to achieve the desired levels of α-cyclodextrin to fat.

This invention also relates to a method for promoting weight loss or reducing body weight gain in a subject comprising administering to a subject in need thereof an amount of α-cyclodextrin sufficient to reduce body weight gain or promote weight loss. A preferred method comprising ingesting sufficient amounts of α-cyclodextrin to complex a desired amount of fat in a fat containing meal, or desired amount of fat per day, to promote weight loss, reduce weight gain or to maintain weight. Preferably the weight loss for a human that is about 1-1.5 lbs/week. An aspect of this invention is a method comprising ingesting sufficient amount of α-cyclodextrin to complex the fat in excess of a desired amount of fat per meal or day that a subject wishes to absorb. The method comprises determining the amount of fat that a subject desires to absorb per meal or per day, determining the amount of ingested fat that in excess of the amount that the subject desires to absorb, and then ingesting sufficient amounts of α-cyclodextrin to complex the excess fat such that only the desired amount of fat is absorbed. For example, based on the disclosure herein that about 1 g of α-cyclodextrin can complex about 9 g of fat, the amount sufficient to promote a weight loss of 1-1.5 lbs/week in a subject consuming a daily diet of 2500 g/day, such diet comprising about 100 g fat/day, the preferred amount of ingested α-cyclodextrin is about 2 g/meal three meals a day. Preferably the total α-cyclodextrin ingested daily is about 500 mg to about 33 g per day, more preferably about 5 g to about 20 g per day, most preferably about 6-11 g/day. Preferably the α-cyclodextrin is administered with a meal such that the ratio of α-cyclodextrin to the ingested fat that one wishes to prevent from being absorbed by the body is about 1:20 w/w to about 1:3 w/w, preferably the ratio is about 1:13 w/w to about 1:5 w/w, more preferably the ratio is about 1:9 w/w. A subject in need thereof is one who is in need of or who wishes to lose weight or inhibit weight gain, e.g., one who is prone to weight gain or one who is already overweight or obese. The subject may also be one who consumes a daily diet comprising about 30% or more fat by calorie. The α-cyclodextrin may be administered to the subject in the form of a powder, a tablet, a capsule, a drink or another delivery medium suitable for consumption, preferably one that does not comprise linolenic acid. The α-cyclodextrin may be administered prior to, concurrently with or subsequent to, ingestion of a fat containing meal. Preferably the α-cyclodextrin is administered just prior to or concurrently with the ingestion of a fat containing meal. More preferably the α-cyclodextrin is administered to a human subject while consuming a fat containing meal. The α-cyclodextrin may be administered in the form of a food product, e.g., bread products, e.g., buns, rolls, or biscuits, or a breakfast cereal, e.g., oatmeal, cream of wheat, raisin bran, corn flakes, or other ready to eat cereal, or preferably in the form of the food products of this invention. The subject may be a mammal, e.g., mouse, rat, cat, dog, cow, horse, monkey, ape or human but preferably human and it is within the skill of the art to adjust the total amounts of α-cyclodextrin administered to the mammal to complex sufficient fat to achieve the desired amount of weight loss. For example, 2 g of α-cyclodextrin per meal reduces the bioavailability of about 18 g of fat per meal or about 54 g of fat per day. This equates to 1-1.5 lbs of body weight per week. This amount of fat represents approximately one-half of the normal daily fat consumption for average-North Americans.

This invention also relates to methods for reducing the bioavailability of fat in a fat containing food product comprising combining an amount of an α-cyclodextrin with a food product such that the food product comprises a ratio of α-cyclodextrin to fat of about 1:20 to about 1:3 w/w, preferably about 1:13 to about 1:5 w/w most preferably about 1:9 w/w. Preferably the total cyclodextrin in the food products of this invention is less than about 9% w/w, more preferably less than about 6% w/w and most preferably less than about 3% w/w. This method may be applied to a variety of fat containing food products, e.g., a farinaceous food product, a prepared vegetable product, a dairy product, a prepared meat or seafood product, gravies, sauces and salad dressings. For example, the farinaceous food product may be a e.g. snack bar, breakfast cereal, pancakes, waffles, muffins, tortillas, corn chips, tortilla chips, snack crackers, breads, cakes, cookies, doughnuts, zeppolies and pies. A dairy product of this invention may be e.g., milk, cream, evaporated or condensed milk, pudding, butter, ice cream, milkshakes, yogurt and drinks prepared with yogurt, e.g., a fruit and yogurt "smoothie", and cheese or processed cheese products or egg products, e.g. an omelet or egg noodles. The vegetable product may be one which is made with fat as one of the ingredients, cream based vegetable soup, soups with meat based stocks, or a vegetable burger, or the vegetable product may be one which is fried in a fat containing material, e.g., french fries, potato chips or falafel, wherein the amount of α-cyclodextrin in the product is based on the estimate of the amount of fat containing material that will be absorbed in the final product. The meat product may be a prepared beef, lamb, pork, poultry or seafood product, e.g., frankfurters, deli slices, sausages, fish sticks, chicken fingers and ground meats to be made into, e.g., hamburgers or meatloaf. The method is also applicable to battered or coated products, e.g., french fries, fish sticks, chicken fingers or tempura, that are fried and to batters that are used to coat products that are fried in a fat containing material. The amount of cyclodextrin in the batter of a batter coated product is based on the estimate of the amount of fat containing material that will be absorbed by the batter coated product. The method is also applicable to candies and condiments, e.g., chocolates, sauces, mayonnaise and salad dressings.

The α-cyclodextrin may be added to the consumable food product at any stage in its production and may be added under conditions that favor formation of complexes of α-cyclodextrin and fat such that the complexes are distributed throughout the consumable food product. Alternatively, the α-cyclodextrin may be combined with a fat containing food product as it is consumed by determining the approximate amount of fat in the food product and then ingesting α-cyclodextrin in amount sufficient to obtain a ratio of ingested α-cyclodextrin to ingested fat of 1:20 to about 1:3, preferably 1:13 to about 1:5 and more preferably about 1:9 w/w. Preferably, the consumable fat containing food product comprises by caloric content 7-80% fat, more preferably 20-70% fat and most preferably 40-70% fat or by weight 5-50% fat, preferably 7-25% fat.

This invention also relates to methods for reducing a pathologic condition often associated with obesity and excess weight, e.g., high cholesterol/HDL ratio, high triglyceride levels, high leptin levels, high insulin levels, and insulin resistance, by administering α-cyclodextrin to a subject in need thereof in sufficient amounts and for sufficient time to reduce the pathologic condition associated with obesity and excess weight.

Serum cholesterol is found in combination with proteins in the blood. Of particular interest are high density (HDL) and low density lipoproteins (LDL). This invention also relates to a method for increasing the level of high density lipoprotein cholesterol(HDL) in a subject comprising administering α-cyclodextrin to a subject in need thereof in an amount sufficient, and for a time sufficient, to increase HDL levels. Preferably the amount of α-cyclodextrin administered to the subject is about 500 mg to about 33 grams per day, preferably about 3-21 g per day and more preferably about 6-11 g per day. The α-cyclodextrin may be administered prior to, concurrently with or subsequent to ingestion of a fat containing meal. The subject may be one who consumes about 100 g fat/day. Preferably the α-cyclodextrin is administered to the subject with a fat containing meal. A sufficient amount of α-cyclodextrin is about 165 mg -11 g/meal, preferably about 1-7 g/meal or more preferably about 2-3.3 g meal. The α-cyclodextrin may be administered in any suitable form, e.g., a tablet, pill, capsules liquid or other delivery medium suitable for human consumption, or in the form of food products, e.g., bread products, buns, rolls, biscuits, and breakfast cereal, e.g., oatmeal, cream of wheat, raisin bran, corn flakes, or other ready to eat cereal, and particularly the food products of this invention. Preferably a serving size of the food product for use in this method contains about 165 mg-11 g/meal, preferably about 1-7 g/meal or more preferably about 2-4 g α-cyclodextrin. Preferably, the α-cyclodextrin is administered to the subject in an amount such that the ratio of α-cyclodextrin to fat of about 1:20 to about 1:3 w/w, preferably about 1:13 to about 1:5 w/w, most preferably about 1:9 w/w per meal, or daily.

It is possible that the total levels of cholesterol in the blood will remain constant even though the levels of HDL are elevated if there is a reduction in levels of LDL. Thus another aspect of this invention is method for increasing HDL levels and reducing LDL levels, reducing the cholesterol/HDL ratio, and or reducing cholesterol levels in a subject in need thereof by administering α-cyclodextrin in an amount and for a time sufficient to increase the HDL levels and/or reduce the LDL levels, decrease the total cholesterol/HDL ratio and/or reduce cholesterol. The reduction in LDL and increase in HDL reduces the total ratio of cholesterol to HDL. Preferably the total cholesterol levels are not substantially reduced or increased.

The α-cyclodextrin may be administered to the subject in the form of a powder, tablet, a capsule, a drink or another delivery medium suitable for consumption, preferably one that does not comprise linolenic acid. A sufficient amount of α-cyclodextrin is about 165 mg-11 g/meal, preferably about 1-7 g/meal or more preferably about 2-3.3 g/meal. Preferably the total α-cyclodextrin ingested daily is about 500 mg to about 33 g per day, more preferably about 5 g to about 20 g per day, most preferably about 6-11 g/day. Preferably the α-cyclodextrin is administered with a meal such that the ratio of α-cyclodextrin to fat is about 1:20 w/w to about 1:3 w/w, preferably the ratio is about 1:13 w/w to about 1:5 w/w, more preferably the ratio is about 1:9 w/w per meal.

A subject in need of increasing the level of HDL and/or reducing LDL Levels, reducing the cholesterol/HDL ratio or reducing cholesterol levels is one who has, or has a predisposition for, a high ratio of total cholesterol to HDL levels. Methods for determining blood cholesterol, HDL and LDL levels are well known in the art and need not be elaborated on herein. However, for a discussion of cholesterol levels and methods for determining cholesterol, HDL and LDL levels (see e.g., Expert Program on detection, evaluation, and treatment of high blood cholesterol in adults. Executive Summary of the Third Report of the National Cholesterol Education Panel on Detection, Evaluation, and Treatment of High Blood Cholesterol in Adults (Adult Treatment Panel III), *JAMA* 285(19); 2486-97:2001, and; *Handbook of Lippoprotein Testing*, Rifai N, Warnick G R and Dominiczak M H, eds. Chapters 9, 11 and 12. AACC Press, Washington D.C., 2000 both incorporated herein by reference.)

This invention also relates to a method of reducing triglycerides in a subject comprising administering to a subject in need thereof an amount of α-cyclodextrin sufficient to reduce triglyceride levels. A subject in need thereof is one who has high triglyceride levels, has a predisposition for high triglyceride levels or has a family history of high triglyceride levels. High triglyceride levels are implicated in a variety of pathological conditions. Thus, this invention also relates to treating a pathological condition, e.g., cardiovascular disease, acute pancreatitis, insulin resistance and uncontrolled diabetes and various dislipidemias associated with high triglyceride levels by administering α-cyclodextrin to a subject in need thereof in an amount sufficient to reduce the levels of triglyerides in the subject. Those of skill in the art are well versed in methods for determining the triglyceride levels in a subject. For a review of methods for determining blood triglyceride levels see e.g., *Handbook of Lipoprotein Testing*, Rifai N, Warnick G R and Dominiczak M H, eds. Chapter 10. AACC Press, Washington, D.C. 2000 incorporated herein by reference. The α-cyclodextrin may be administered prior to, concurrently with or subsequent to ingestion of the fat containing meal. More preferably the α-cyclodextrin is administered to the subject with a fat containing meal. A sufficient amount of α-cyclodextrin is about 165 mg-11 g/meal, preferably about 1-7 g/meal or more preferably about 2-4 g meal. Preferably the total α-cyclodextrin ingested daily is about 500 mg to about 33 g per day, more preferably about 5 g to about 20 g per day most preferably about 6-11 g/day. Preferably the α-cyclodextrin: fat ratio ingested per meal or daily is about 1:20 to about 1:3 w/w, preferably the ratio is about 1:13 to about 1:5 w/w and more preferably the ratio is about 1:9 w/w. The α-cyclodextrin may be administered to the subject in the form of a powder, tablet, a capsule, a drink or another delivery medium suitable for consumption, preferably one that does not comprise linolenic acid. The α-cyclodextrin may be administered to the subject in the form of a food product, particularly a food product of this invention.

This invention further relates to a method for reducing leptin levels in a subject comprising administering α-cyclodextrin to a subject in need thereof in an amount sufficient to reduce leptin levels in the subject. The α-cyclodextrin may be administered prior to, concurrently with or subsequent to ingestion of the fat containing meal. Preferably the α-cyclodextrin is administered just prior to or concurrently with the ingestion of the fat containing meal. More preferably the α-cyclodextrin is administered to the subject with a fat containing meal. The amount of α-cyclodextrin ingested per meal is preferably about 165 mg-11 g/meal, more preferably 1-7 g/meal and most preferably 2-3.3 g/meal. Preferably the total α-cyclodextrin ingested daily is about 500 mg to about 33 g per day, more preferably about 5 g to about 20 g per day most preferably about 6-11 g/day. Preferably the amount of α-cyclodextrin administered daily to the subject and fat ingested daily by the subject is in a ratio of about 1:20 to about 1:3 w/w, preferably the ratio is about 1:13 to about 1:5 w/w and more preferably the ratio is about 1:9 w/w. A subject in need of reducing leptin is one who has high leptin levels, has a predisposition for leptin resistance. Leptin levels can be determined using any method known in the art for determining leptin levels. For a review of various assays for determining leptin resistance see e.g., Maffei et al., *Nature Med* 1:1155-1161 (1995) incorporated herein by reference. The α-cyclodextrin may be administered to the subject in the form of a powder, tablet, capsule, drink, confection or other delivery medium suitable for human consumption, preferably one that comprises less that 2% linolenic acid, more preferably one that comprises less than 0.2% linolenic acid and most preferably one that does not comprise linolenic acid. The α-cyclodextrin may be administered to the subject in the form of a food product, preferably a food product of this invention.

This invention further relates to a method for reducing blood insulin levels and insulin resistance in a subject comprising administering α-cyclodextrin to a subject in need thereof in an amount sufficient to reduce blood insulin levels in the subject. Insulin resistance is typically the cause of Type II diabetes. Insulin resistance can be estimated by triglyceride/HDL-cholesterol ratios and glucose/insulin ratios. A subject in need thereof is one who displays high insulin levels, has Type II diabetes or who has a predisposition for developing Type II diabetes or who has a family history of high insulin levels or Type II diabetes. Any method used routinely for determining insulin levels can be used herein to assay and monitor insulin levels and resistance. See for example Berson et al. (Eds) *Methods in Investigative and Diagnostic Endocrinology*, ch 3, Part III, Vol. 28. American Elsevier Publishing Co., New York, 1973, incorporated herein by reference, for a description of assays for determining insulin levels. The α-cyclodextrin may be administered prior to, concurrently with or subsequent to ingestion of the fat containing meal. Preferably the α-cyclodextrin is administered just prior to or concurrently with the ingestion of the fat containing meal. More preferably the α-cyclodextrin is administered to the subject with a fat containing meal. The amount of α-cyclodextrin ingested per meal is preferably about 165 mg -11 g/meal, more preferably about 1-7 g/meal and most preferably about 2-3.3 g/meal. The total α-cyclodextrin ingested daily is about 500 mg to about 33 g per day, preferably about 5 g to about 20 g per day and more preferably about 6-11 g/day. Preferably the amount of α-cyclodextrin administered daily to the subject is based on the fat ingested daily by the subject and is in a ratio of about 1:20-1:3 w/w, preferably the ratio is about 1:13-1:5 w/w and more preferably the ratio is about 1:9 w/w. The α-cyclodextrin may be administered to the subject in the form of a powder, tablet, a gel, capsule, a liquid or another delivery medium suitable for human consumption, preferably one that does not comprise linolenic acid. The α-cyclodextrin may be administered to the subject in the form of a food product, preferably a food product of this invention.

This invention also relates to a method for reducing diarrhea in a subject in need thereof comprising administering to a subject in need thereof α-cyclodextrin in an amount and for a time sufficient to reduce diarrhea in the subject. The subject may be a mammal, e.g., mouse, rat, cat, dog, cow, horse, monkey, ape or human. Such a subject may be one who is prone to diarrhea, or is currently suffering from diarrhea, e.g., the subject may be a cholecystectomy patient prone to or having diarrhea, a patient suffering from fat aggravated diarrhea, or a patient having acute or subacute diverticulitis, the acute phases of certain inflammatory conditions of the bowel, e.g., ulcerative colitis or Crohn's disease and after some types of intestinal surgery, e.g., a colostomy or ileostomy. The α-cyclodextrin maybe administered in the form of a food product, preferably a food product of this invention for example a farinaceous or non-farinaceous food product of this invention. The α-cyclodextrin may also be administered to the subject in the form of a powder, tablet, a capsule, a gel, a liquid or another delivery medium suitable for consumption. The α-cyclodextrin may be administered with a meal at about e.g. 165 mg-11 g/meal, preferably about 1-7 g/meal and more preferably about 2-3.3 g/meal. Preferably the total α-cyclodextrin ingested daily is about 500 mg to about 33 g per day, more preferably about 5 g to about 20 g per day, most preferably 6-11 g/day. The ratio of ingested α-cyclodextrin to ingested fat per meal, or daily, preferably per meal, is about 1:20-1:3 w/w, preferably the ratio is about 1:13-1:5 w/w, more preferably the ratio is about 1:9 w/w. The α-cyclodextrin may be administered prior to, concurrently with or subsequent to ingestion of the fat containing meal. Preferably the α-cyclodextrin is administered just prior to or concurrently with the ingestion of the fat containing meal.

The addition of α-cyclodextrin to a pet food product maintains or promotes good feces quality of a pet and/or improves feces quality of a pet Good quality pet feces is a very desirable trait as perceived by the pet owner in that it is not only generally more aesthetically pleasing but is also an indicator of good pet health. As such, this invention is also related to a pet food product which comprises α-cyclodextrin in an amount sufficient to maintain or promote good feces quality of a pet and/or improve the feces quality of a pet. Feces having good quality are firm and well formed maintaining their shape. A feces with a moisture content such that the shape is not maintained (loose stools or diarrhea) or a moisture content such that the feces are hard and dry, are not good quality feces. The pet food is preferably a packaged pet food. The packaging may be plastic, paper, cardboard or metal, e.g. tin or flexifoil. The pet food may be a moist pet food, such as those packaged in cans or flexifoil or a dry pet food such as those packaged in paper or cardboard, e.g., kibble or biscuits. Preferably the pet food is a food developed for a cat, dog, cow or horse. This invention also relates to a method for maintaining or promoting good feces quality of a pet and/or improving feces quality of a pet by administering α-cyclodextrin to a pet, preferably a pet in need thereof, in an amount and for a time sufficient to maintain or promote good feces quality of the pet and/or to improve feces quality of a pet. The α-cyclodextrin may be administered with a meal at about e.g. 165 mg-11 g/meal, preferably about 1-7 g/meal and more preferably about 2-3.3 g/meal. Preferably the total α-cyclodextrin ingested daily is about 500 mg to about 33 g per day, more preferably about 5 g to about 20 g per day, most preferably 6-11 g/day. The ratio of ingested α-cyclodextrin to ingested fat per meal, or daily, preferably per meal, is about 1:20-1:3 w/w, preferably the ratio is about 1:13-1:5 w/w, more preferably the ratio is about 1:9 w/w. The α-cyclodextrin may be administered prior to, concurrently with or subsequent to ingestion of the fat containing meal. Preferably the α-cyclodextrin is administered just prior to or concurrently with the ingestion of the fat containing meal. The α-cyclodextrin may be administered to the pet in the form of a pill, wafer, tablet capsule etc or in the form of a pet food product, particularly a pet food product of this invention, including moist pet foods such as that packaged in a can or flexifoil or a dry pet food such as those packaged in a paper or cardboard container e.g. a kibble or biscuit. A pet in need thereof is one having poorly formed feces or having a predisposition to have poorly formed feces, e.g. a pet with diarrhea or having a predisposition to diarrhea.

In the methods of this invention, the α-cyclodextrin may be administered in the form of a single dosage unit consisting essentially of α-cyclodextrin. The single dosage unit may be in the form of a powder, tablet, capsule, gel, pellet, liquid, etc., the α-cyclodextrin may be incorporated into a powder, tablet, capsule, gel, pellet, liquid, etc by any means that is routinely used in the art. The α-cyclodextrin may be incorporated into the powder, tablet, gel, capsule, pellet, liquid, etc. with other commonly used additives, e.g. colorants, anti-oxidants, fillers, starches, sugars, anti-bacterial or anti-fungal agents, preservatives, stabilizers or emulsifiers. The α-cyclodextrin may be combined with any pharmaceutical carrier acceptable for oral administration, e.g. it may be enclosed in a hard or soft shell gelatin capsule, compressed into tablets, or incorporated directly into the individual's diet. Specifically, α-cyclodextrin may be incorporated with excipients and used in the form of digestible tablets, capsules, elixirs, suspensions, syrups, wafers, and the like. The α-cyclodextrin may be mixed with other food forms and pharmaceutically acceptable flavor enhancers. Suitable pharmaceutical carriers and formulations are described, for example, in Remington's Pharmaceutical Sciences (19th ed.) (Genarro, ed. (1995) Mack Publishing Co., Easton, Pa.), incorporated herein by reference. Preferably the formulation is such that the α-cyclodextrin is released in the stomach to mix with the ingested food so that complexes of α-cyclodextrin and fat are formed such that the α-cyclodextrin: fat complexes are already formed when the chyme is pushed into the jejunum and is mixed with bicarbonate and lipase.

Because only a relatively small amount of total cyclodextrin (e.g. less than about 9% w/w preferably less than about 6% w/w, more preferable less than about 3% w/w) is added to food products to achieve the desired α-cyclodextrin to fat ratio, the α-cyclodextrin may be added to a food composition rather than using α-cyclodextrin as a filler to replace an equal amount of the dry ingredients in the food product. Thus the caloric content of the food products of this invention as determined by bomb calorimetry is not substantially altered by the addition of total cyclodextrin. Even if dry ingredients are removed from the food product to compensate for the relatively small amount of cyclodextrin added to the food product (less than about 9% preferably less than about 6% w/w, more preferably less than about 3% w/w) the caloric content of the food would not be substantially reduced.

This invention also relates to methods for enhancing organoleptic properties of a fat containing consumable food product without reducing the caloric content (as assayed by bomb calorimetry) or substantially reducing the percentage of fat in the food product. The method comprises adding α-cyclodextrin to the fat containing food product during the preparation of the product. The amount of α-cyclodextrin added to the foods is based on the amount of fat in the finished product. The food products of this invention typically have a ratio of α-cyclodextrin to fat of about 1:20-1:3 w/w, preferably about 1:13-1:5 w/w, and more preferably about 1:9 w/w. The total amount of cyclodextrins added to the product is typically less than 9% w/w, preferably less than 6% w/w and more preferably less than 3% w/w. Products made with as low as 0.7% w/w α-cyclodextrin have enhanced organoleptic properties, e.g. a sweeter taste and a smoother texture. The consumable fat containing food product may comprise by calorie content 7-80% fat, preferably 20-70% or more preferably 40-70% fat or by weight 5-50% w/w fat or preferably 7-25% w/w fat. This method may be applied to a variety of fat containing food products, e.g., a farinaceous food product, a prepared vegetable product, a dairy product, a prepared meat poultry or seafood product, soups and condiments e.g., gravies, sauces, mayonnaise, salad dressing etc. For example, the farinaceous food product may be e.g., a snack bar, breakfast cereal, pancake, waffle, muffin, tortilla, corn chips, tortilla chips, snack cracker, bread, cake, cookie, doughnut zeppoli and pie or other fruit or nut filled baker product. A dairy product of this invention may be e.g., milk, cream, evaporated or condensed milk, pudding, butter, ice cream milkshakes, and cream based sauces or soups, yogurt and drinks prepared with yogurt, e.g., a fruit and yogurt "smoothie", and cheese or processed cheese products, or egg products, e.g., an omelet or egg noodles. The vegetable product may be one which is made with fat as one of the ingredients, e.g., hummus, tahini, margarine and nut butters, or may be one which is fried in a fat containing material, e.g., french fries, vegetable tempura, or falafel, wherein the amount of a α-cyclodextrin in the fried product is based on the amount of fat containing material that is estimated to be contained in the fried food product after frying. The meat product may be a prepared beef, lamb, pork, poultry or seafood product, e.g., frankfurters, deli slices, sausages, fish sticks, chicken fingers and ground meats to be made into, e.g., hamburgers, meatballs or meatloaf. The method is also applicable to batters that are used to coat products, e.g., french fries or tempura, for frying in a fat containing material, e.g., lard or oil. In addition the method is applicable to soups, and condiments, e.g., gravies, sauces and salad dressing, wherein the α-cyclodextrin to fat ratio described supra may enhance the texture and/or flavor of the product. The products of this invention often taste comparable to a like product made without α-cyclodextrin and/or they have a smoother texture and a sweeter taste. In addition, the inclusion of α-cyclodextrin in evaporated or condensed milk produces a whiter product as compared to a like product without the α-cyclodextrin.

This invention also relates to a method for reducing the amount of time required to prepare whipped cream comprising adding α-cyclodextrin to cream prior to or during whipping. The α-cyclodextrin is added in an amount sufficient to reduce the amount of time required to form whipped cream. Preferably the amount of α-cyclodextrin is sufficient to attain a ratio of α-cyclodextrin to fat in the cream of about 1:20-1:3 w/w, preferably about 1:13-1:5 w/w and more preferably about 1:9 w/w. Reducing the amount of time required for whipped cream to form reduces the amount of power needed to run a mixer, which when calculated on a commercial scale results in a large monetary savings in both electricity and manpower. The whipped cream remains soft and scoopable and the whey does not separate from the rest of the components.

It is envisioned herein that the α-cyclodextrin-containing whipped cream may be used as a topping on another fat containing material that may or may not contain α-cyclodextrin and the amount of α-cyclodextrin in the whipped cream would be sufficient to complex the fat in the other fat containing material when consumed thus reducing its bioavailability as well.

EXAMPLES

Example 1

Figure 9A:
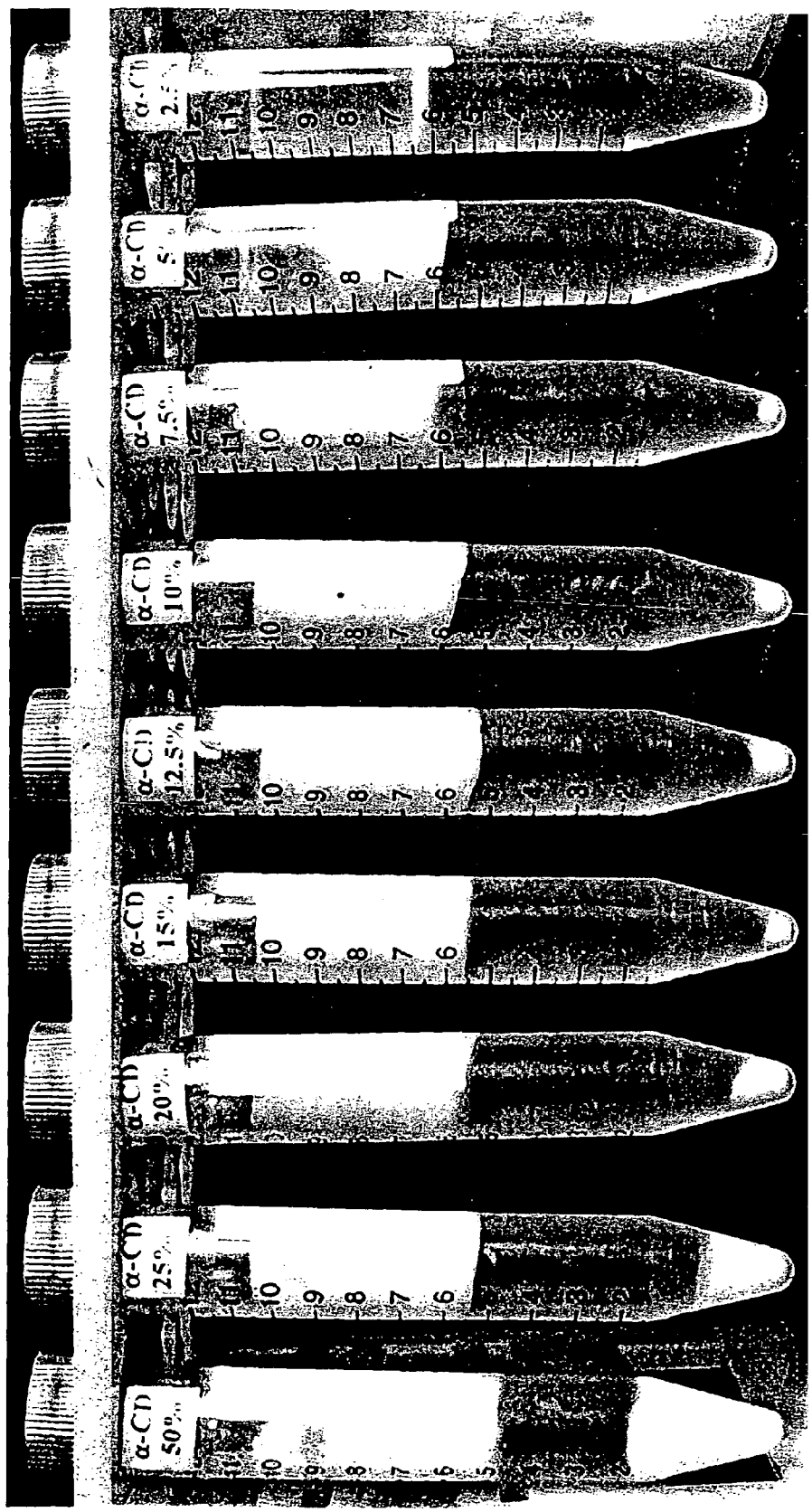
FIG. 9A-9C depicts the results of an in vitro study of vegetable oil (4 g), water (6 g) (with added food coloring for contrast) and varying amounts of (A) α-cyclodextrin (100-2,000 mg, right to left), (B) α-cyclodextrin or (C) γ-cyclodextrin. A band of "wax-like" material layered between the oil and aqueous phases is apparent in the tubes. The size of this band increases with increasing amounts of α-cyclodextrin to a maximum in the tube labeled 10% (400 mg α-cyclodextrin/4 g oil). Note the increasing size (right to left) of a white layer of un-reacted α-cyclodextrin in the bottom of the tubes. This material is displaced from solution by either the oil or the α-cyclodextrin-oil complex. These tubes were centrifuged in order to improve the definition of the layers. The "wax-like" complex is of such a consistency that all of the tubes except for the furthest two to the right can be inverted without leakage of the aqueous phase around the complex.
Figure 9B:
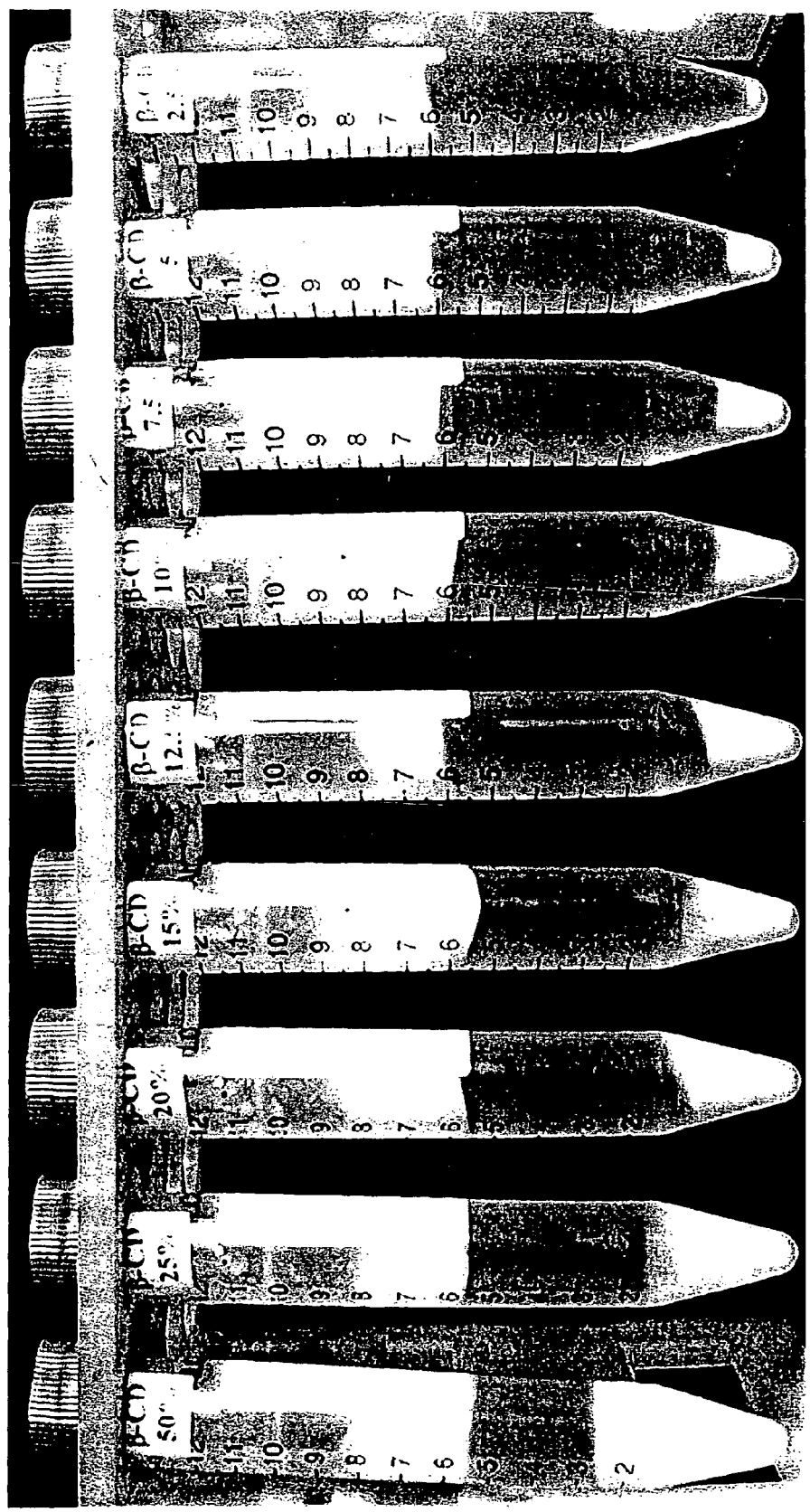
Figure 9C:
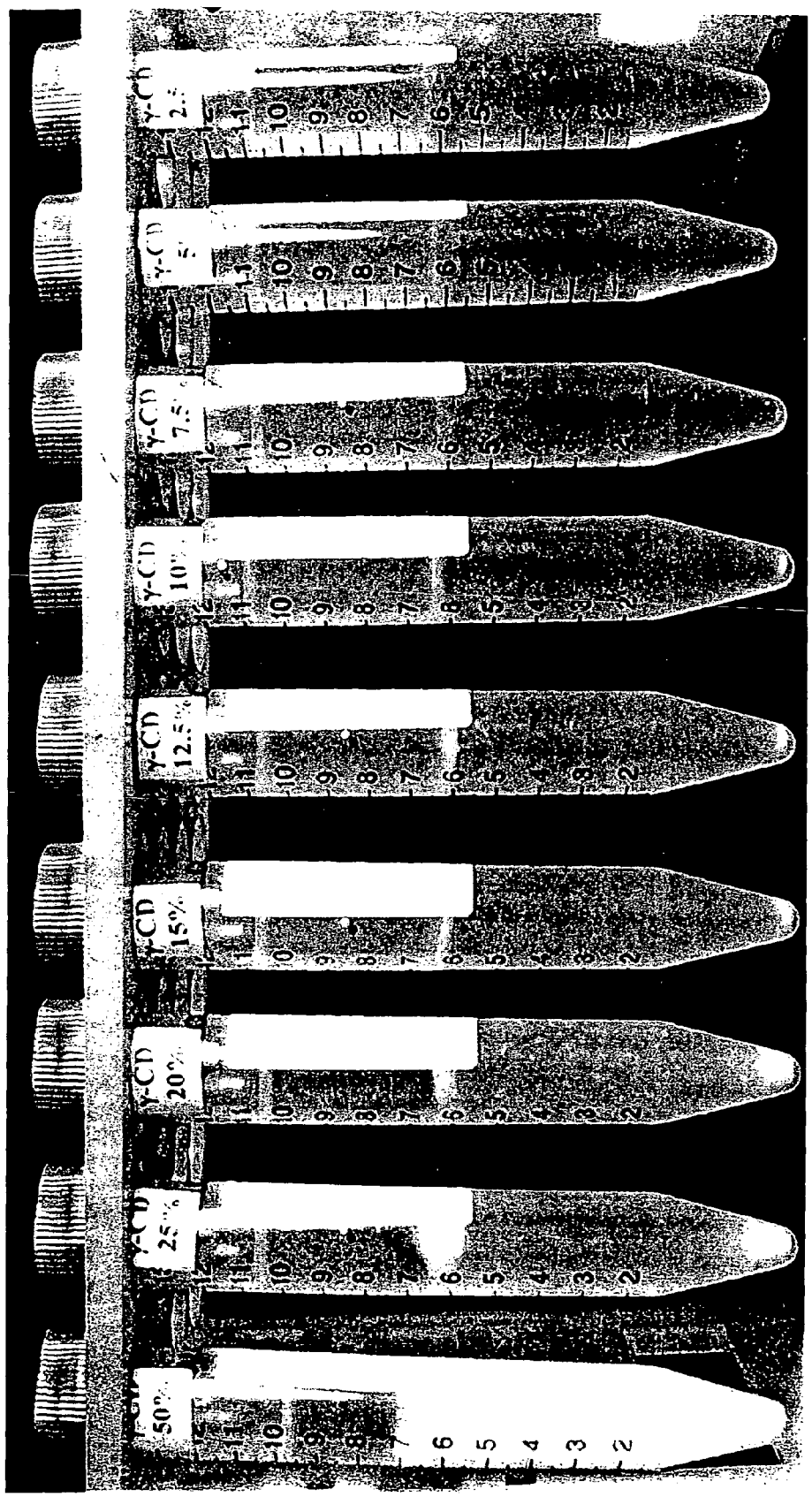

FIGS. 9A-9C depict the results of an in vitro study of vegetable oil (4 g), water (6 g) (with added food coloring for contrast) and varying amounts of (A) α-cyclodextrin (100-2,000 mg, right to left), (B) β-cyclodextrin or (C) γ-cyclodextrin. A band of "wax-like" material layered between the oil and aqueous phases is apparent in the tubes. The size of this band increases with increasing amounts of α-cyclodextrin to a maximum in the tube labeled 10% (400 mg α-cyclodextrin/4 g oil). Note the increasing size (right to left) of a white layer of un-reacted α-cyclodextrin in the bottom of the tubes. This material is displaced from solution by either the oil or the α-cyclodextrin-oil complex. These tubes were centrifuged in order to improve the definition of the layers. The "wax-like" complex is of such a consistency that all of the tubes in 9A except for the furthest two to the right can be inverted without leakage of the aqueous phase around the complex.

The pore size of α-cyclodextrin is significantly smaller than the pore size of β-cyclodextrin and γ-cyclodextrin. Thus one would not have expected α-cyclodextrin to complex triglyceride molecules because the molecules would not fit within the pore of the α-cyclodextrin. However, the amount of complexed fat in the tubes containing the oil/β-cyclodextrin (FIG. 9B) and oil/γ-cyclodextrin mixture (FIG. 9C) is significantly less than seen in the tubes containing the oil/α-cyclodextrin mixture (FIG. 9A). This difference is even more dramatic in FIG. 9C wherein a band of wax-like material is bearly noticeable. The white substance in the bottom of the tubes is precipitated cyclodextrin.

Example 2

Animal Studies

To examine the effect of α-cyclodextrin on body weight gain and plasma lipid levels in animals fed high fat and low fat diets, we conducted a short-term feeding study using Wistar rats. Forty-two male Wistar rats, 10 weeks old, were obtained from Harlan-Sprague Dawley. Following a one-week adaptation while being fed the control low fat diet (LF), they were divided equally into two groups, one low-fat (LF) diet and the other high-fat (HF) diet. These two groups were further divided into two subgroups. Two groups were fed the LF or HF diet and served as controls for the other two test groups which were fed the LF or HF diet containing α-cyclodextrin, wherein the amount of α-cyclodextrin was such that the ratio of α-cyclodextrin to fat in the food was 1:10 w/w. The LF diet was formulated according to AIN-93M diet and contains 4% (w/w) soybean oil as the fat source. The HF diet was a modification of the LF diet with 40% soybean oil. Therefore, the LF group receiving α-cyclodextrin (LF-cyclodextrin) ingested 0.4 g of α-cyclodextrin/100 g of food and the HF group receiving α-cyclodextrin (HF-cyclodextrin) ate 4 g α-cyclodextrin/100 g of food. The caloric density of the 4 diets were: LF: 3.96 kcal/g; LF-cyclodextrin: 3.66 kcal/g; HF: 5.70 kcal/g; HF-cyclodextrin: 5.59 kcal/g.

The rats were housed as pairs for five weeks prior to being placed in individual metabolic cages for the sixth week of the study. All of the rats' feces were collected during the final three days of the study. At the end of the sixth week of the study period the rats were sacrificed by decapitation after a brief exposure to carbon dioxide gas. Trunk blood and the livers were collected from each animal. The rest of the body was eviscerated and all visible fat from the internal cavity was collected and weighed. The carcass was frozen for body composition analysis at a later date.

Food and Energy Intake:

The amount of food ingested by the animals was monitored for the first five weeks of the study and from these data the caloric intake was calculated. These data are presented in Table 1 and FIGS. 1 and 2 as an average for each group ±SD.

TABLE 1

Total food and caloric intake of 4 groups of rats during the first 5 weeks of the study (mean ± SD).

| Group | Total Food Ingested (g) | Caloric Intake (Kcal) |
|---|---|---|
| LF | 779 ± 40 | 2,970 ± 154 |
| LF-cyclodextrin | 786 ± 87 | 2,978 ± 332 |
| HF | 753 ± 70 | 4,072 ± 921 |
| HF-cyclodextrin | 769 ± 107 | 3,986 ± 560 |

There was no statistical difference amongst any of the groups with regards to the amount (g) of food ingested. Due to the higher caloric content of the HF diet, rats in the 2 HF groups consumed significantly more calories compared to that of the 2 LF fed groups. It should be noted that caloric intake between the two HF groups or the two LF groups was not affected by the ingestion of α-cyclodextrin. These data demonstrate that (1) all of the rats were satiated by the amount of the food ingested, and (2) that if the α-cyclodextrin was complexing a portion of the fat and thus preventing the fat from being digested by the rats, the rats were not consuming more food to compensate for it. There is no statistical difference amongst the groups as it pertains to water consumption.

Figure 2:
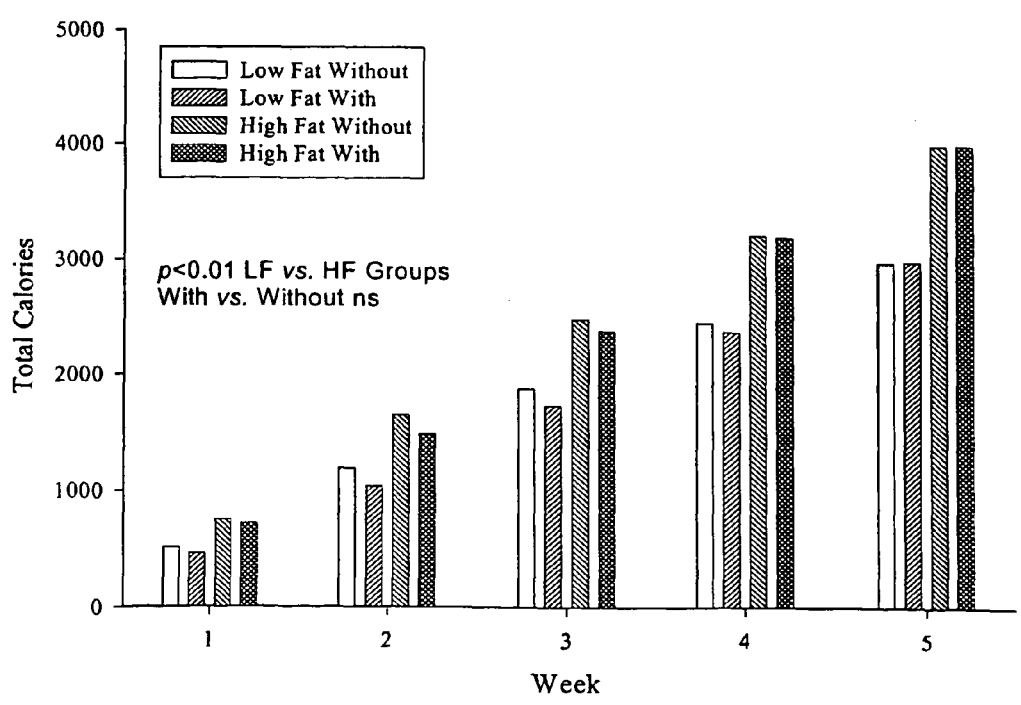
FIG. 2 depicts the cumulative caloric intake of the four groups of rats and indicates that there was no significant difference in the calories of food that the two pairs of rats (low fat and high fat) consumed.
Figure 3:
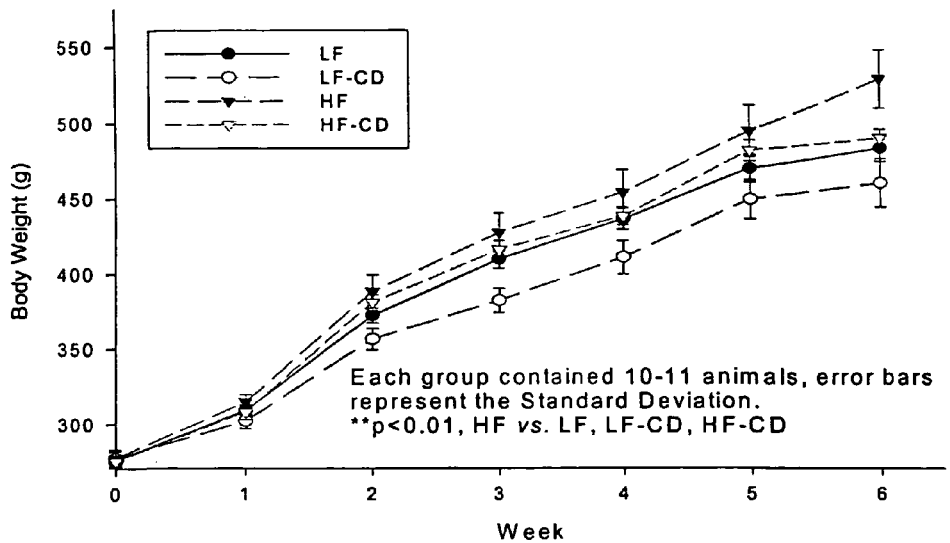
FIG. 3 illustrates the change in body weight of the four groups of adult rats during the entire study period.

Body Weight Change:

FIG. 1 illustrates the change in body weight of the four groups of growing, rats during the entire study period. As we have previously demonstrated (Jen *Physiol Behav* 42:551-556 (1988) and Jen et al. *Int J Obesity* 19:699-708 (1995) incorporated herein by reference) those animals receiving the HF diet gained more weight than did those receiving the LF diet. Interestingly FIG. 3 demonstrates that those animals receiving diet comprising α-cyclodextrin and fat at a ratio of 1:10 w/w pained weight at a slower rate relative to their respective control groups. Although the control group on the HF diet appears to still be gaining weight at a significant rate, the rate of weight gain of the other three groups appear to have reached a plateau. In this example the animals fed the α-cyclodextrin/high fat diet appear to have gained weight at nearly an identical rate as the animals receiving the low fat diet (4% w/w fat) without α-cyclodextrin. Thus by adding α-cyclodextrin to the diet the animals wherein the amount of α-cyclodextrin is based on the amount of fat in the diet, in this example 4% w/w α-cyclodextrin and 40% w/w fat, the rate of weight gain is significantly inhibited. This is in sharp contrast to previous studies wherein a cyclodextrin composition was added to rat diets did not exert an effect on the rate of weight gain until the percentage of the cyclodextrin composition in the food was at least 58.5% w/w.

Body Composition:

Body composition analysis reveals that adding α-cyclodextrin to the LF diet did not affect body fat content. However, when α-cyclodextrin was added to the HF diet, it significantly reduced body fat mass (LF: 48.3±2.4 g; LF-cyclodextrin: 51±6.5 g; HF: 71.3±5.8 g; HF-cyclodextrin: 55.6±2.4 g, mean±SE). This implies that α-cyclodextrin is most effective at reducing body fat when the dietary fat is high.

Stoichiometry:

Shimada et al. (Shimada et al. "Structure of inclusion complexes of cyclodextrins with triglyceride at vegetable oil/water interface" *J. Food Sci.* 1992; 57(3):655-656) have reported that two molecules of α-cyclodextrin complex with one free fatty acid (FFA) while Szejtli (Szejtli J. "Utilization of cyclodextrins in industrial products and processes" *J. Mater. Chem.* 1997;7:575-587) suggests that this phenomenon is dependent upon the chain length of the fatty acids and that it is possible for 3-4 molecules of α-cyclodextrin to complex with each of the three fatty acids of a triglyceride molecule. These results suggest 9-12 molecules of α-cyclodextrin would be required to completely complex one molecule of triglyceride. If this were the case it would be difficult to imagine being able to feed enough of the α-cyclodextrin to an animal in order to complex sufficient triglycerides to make a significant difference in body weight as triglycerides and α-cyclodextrin have similar molecular weights. However, from the data disclosed herein wherein e.g., a diet comprising 4% α-cyclodextrin and 40% fat inhibits weight gain and reduces body fat mass, as the molecular weights are very similar, we have calculated that one α-cyclodextrin molecule can complex approximately nine molecules of triglyceride, the equivalent of 27 free fatty acids. Thus we can convert this directly to 1 gram of α-cyclodextrin complexes approximately 9 grams of triglyceride. Without wishing to be bound by theory, the difference in the ratio of α-cyclodextrin molecules needed to complex a triglyceride based on the disclosure of Shimada or Szejtli and the ratio of α-cyclodextrin to fat disclosed herein as forming complexes with fat suggest that the α-cyclodextrin catalyzes the formation of large particles of triglyceride coated with α-cyclodextrin in the form of a very stable micelle, thus reducing the bioavailability of the fats in those particles. We have been able to demonstrate that when purified olive oil is premixed with α-cyclodextrin the lipolytic activity of porcine pancreatic lipase is significantly reduced. As these particles are formed in the midst of chyme, a very complex "soup", the particles may be analogous to lipoprotein particles of the blood stream. This would also explain why the bacterial flora do not appear to be able to metabolize the α-cyclodextrin fat complexes coming from the small intestine.

Figure 4:
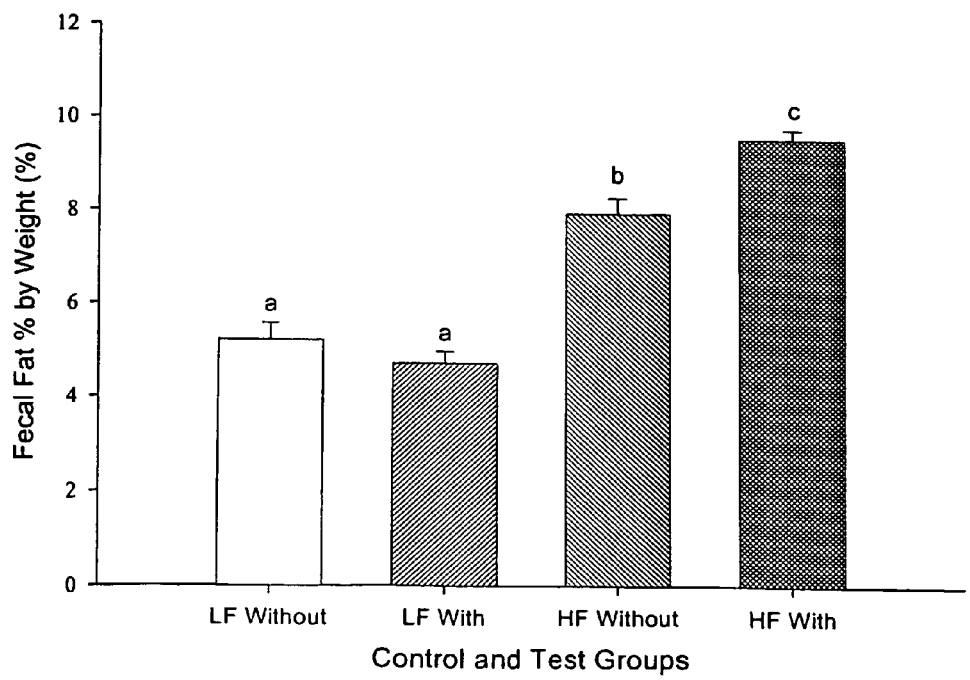
FIG. 4 depicts the fecal fat content of four groups of rats. Groups sharing a common superscript are not significantly different.

Fecal Fat Content:

Total lipid determinations were performed on the collected feces using standard techniques Folch et al. *J Biol. Chem* 226: 497-509 (1957) incorporated by reference. The results (FIG. 4) indicate a significant increase in fecal fat in HF-cyclodextrin (p<0.05) but not in LF-cyclodextrin fed rats. On average this increase was approximately 25%. These data indicate that the α-cyclodextrin reduced the bioavailability of the fat by preventing the fat from being absorbed when fat intake is high, and, furthermore, prevented it from being metabolized by the intestinal flora of the animals' large bowel. The latter observation was confirmed by visual inspection of the feces. All of the collected material appeared to be of normal shape and consistency; there was no indication of diarrhea.

Figure 5:
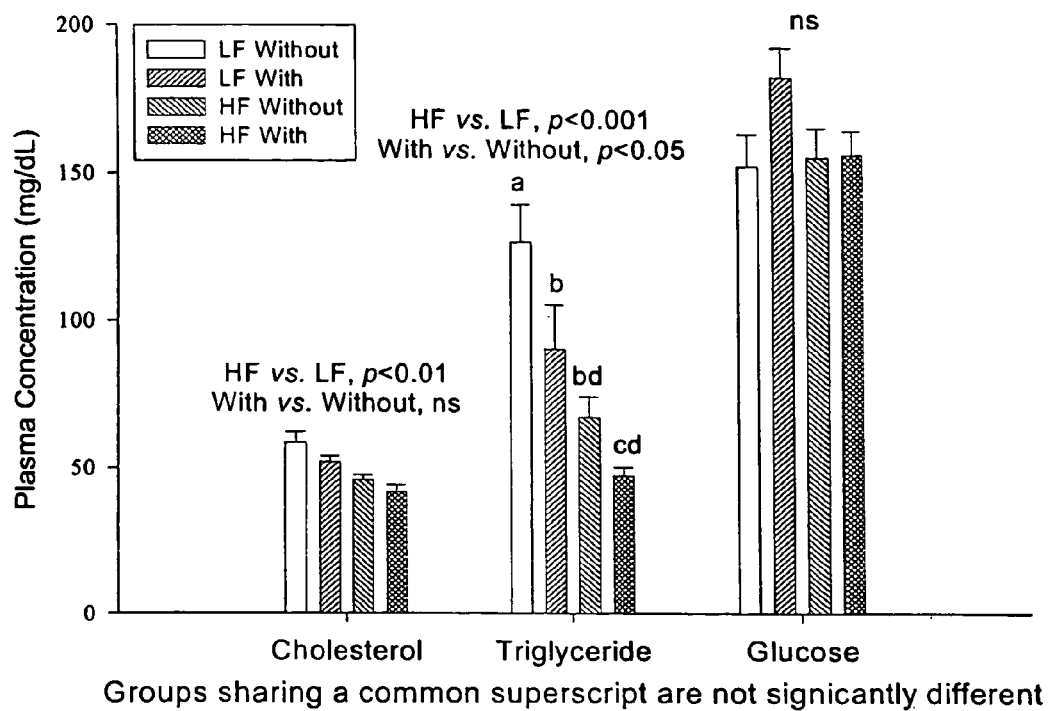
FIG. 5 depicts the blood plasma parameters of four groups of rats at sacrifice. The plasma glucose, cholesterol and triglyceride concentrations were measured on all of the animals.

Plasma Glucose, Cholesterol and Triglyceride Levels:

The plasma glucose, cholesterol and triglyceride concentrations were measured on all of the sacrificed animals using standard clinical laboratory techniques as may be found in Tietz Textbook of Clinical Chemistry, second edition. Burtis C A and Ashwood E R eds., W. B. Saunders Company A Division of Harcourt Brace & Company, 1994, Philadelphia incorporated herein by reference. (FIG. 5). On average the α-cyclodextrin appeared to have decreased the plasma total cholesterol levels by about 10%. This decrease was not statistically significant over this short study period; we expect that with longer feeding period, cholesterol levels will continue to decline. The HDL cholesterol was also decreased but by a lesser extent, approximately 6-8%. LDL cholesterol levels on all of the animals were too low to measure reliably since in rats the majority of the cholesterol is carried in the HDL-cholesterol fraction, and very little is carried in the LDL-cholesterol fraction. The triglyceride levels were significantly reduced (p<0.05) by about 30% in the animals that received the α-cyclodextrin. Glucose levels were not affected significantly by HF or α-cyclodextrin feeding in contrast to the results reported in Japanese Patent application S60-94912 wherein the high levels of cyclodextrins (19.5%, 39%, 58.5% or 78% w/w CD:total food) reduced blood glucose significantly.

Insulin Resistance:

Increased insulin resistance, elevated blood triglycerides and reduced HDL cholesterol levels are all the risk factors of Syndrome X. Insulin/glucose ratios as well as triglyceride/HDL ratios were calculated to provide indications about insulin resistance and risk of Syndrome X. (Szejtli J. Mater. Chem. 1997;7:575-587 incorporated herein by reference). Although, due to the short period of the study, HF feeding did not significantly induce insulin resistance there did appear to be a trend in that direction. Similarly, the HF-cyclodextrin animals showed a trend towards reduced insulin resistance. We expect based on the human data presented below that when the feeding period is lengthened insulin resistance will become significant and that α-cyclodextrin may significantly reduce the insulin resistance seen in HF fed rats. The reduction in triglyceride/HDL cholesterol ratios by α-cyclodextrin indicated a significant decrease in the risk for Syndrome X.
Leptin:

Leptin is a protein hormone with important effects in regulating body weight, metabolism and reproductive function. Leptin is secreted predominantly by adipocytes, supporting the idea that body weight is sensed as the total mass of fat in the body. Thus we analyzed the plasma leptin levels in the animals fed the LF and HF diets ±α-cyclodextrin using standard techniques.

Figure 6:
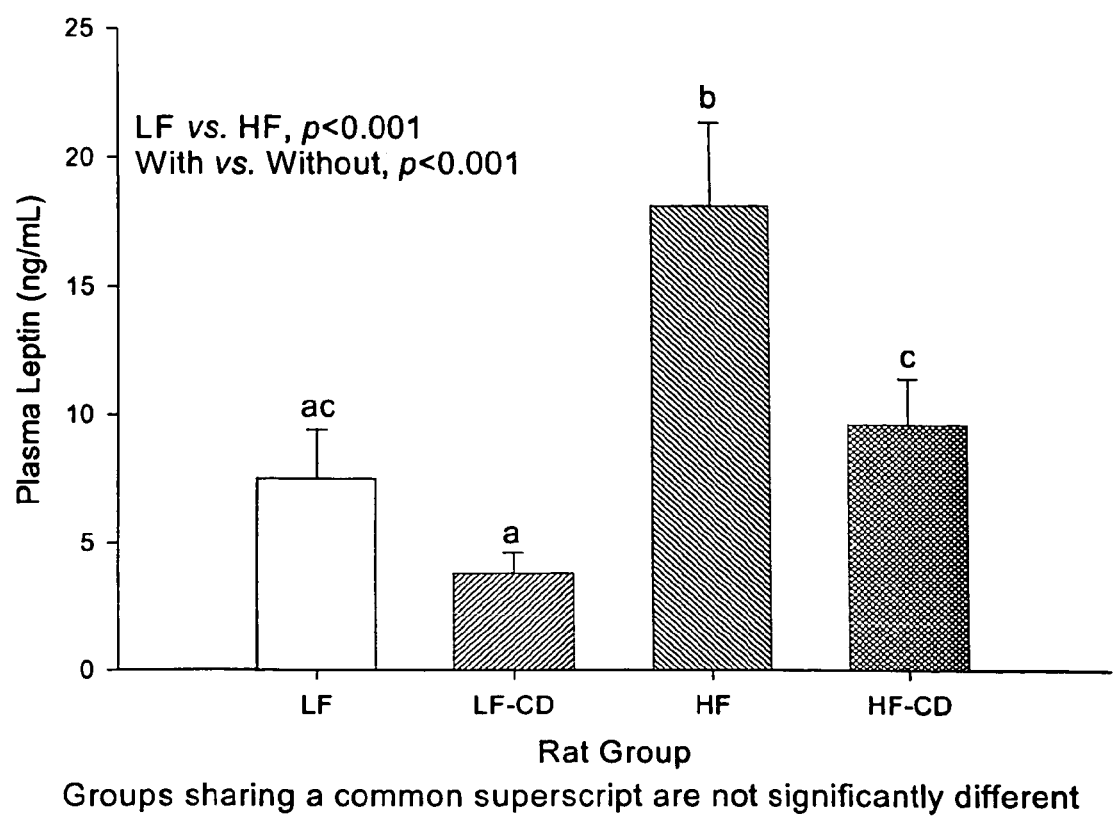
FIG. 6 compares the plasma leptin values obtained from the four groups of rats.

FIG. 6 compares the plasma leptin values obtained from the four groups of rats wherein leptin levels were determined by using an RIA rat leptin kit (Linco Research, St. Charles, Mo.) following manufacturers instructions, incorporated here in by reference. The amount of leptin present in the plasma of the HF rats (18.1±3.2 ng/mL) is statistically higher ($p<0.001$) than that of the LF rats (7.5±1.9 ng/mL). The plasma leptin concentration of the HF-cyclodextrin rats (9.6±1.8 ng/mL) is not statistically different from the LF rats. As adipose is the source tissue for leptin the data suggests that there is more body fat in the HF rats relative to the other three groups. Since leptin reduces food intake and body weight, the higher levels of leptin indicate a state of leptin resistance in these HF fed rats. However, when α-cyclodextrin was added to the HF diet, rats consuming this diet had significantly lower leptin levels. This demonstrates that body fat mass was reduced in HF-cyclodextrin rats, and suggests leptin resistance in these rats is reduced. These results suggest that these rats are more sensitive to the effects of leptin and therefore future weight regain may be more difficult. When leptin per gram of adipose tissue was calculated, it was revealed that both diet fat and α-cyclodextrin had independent effects on blood leptin levels (LF: 0.11±0.02 ng/mL/g of adipose tissue; LF-CD: 0.075±0.01; HF: 0.24±0.03; HF-CD: 0.17±0.03; diet effect $p<0.001$; CD effect $p<0.001$). In rats fed the HF diet with added α-cyclodextrin, the reduction in blood leptin level was more than that which can be accounted for by the reduction of body fat mass. Therefore, α-cyclodextrin reduces blood leptin levels and reduces leptin resistance in addition to that induced by reduced body weight/fat. Similar results were obtained in human studies (see Example 4).

Example 3

Initial Clinical Data

Effect of α-Cyclodextrin on Serum Triglyceride Levels

Figure 7:
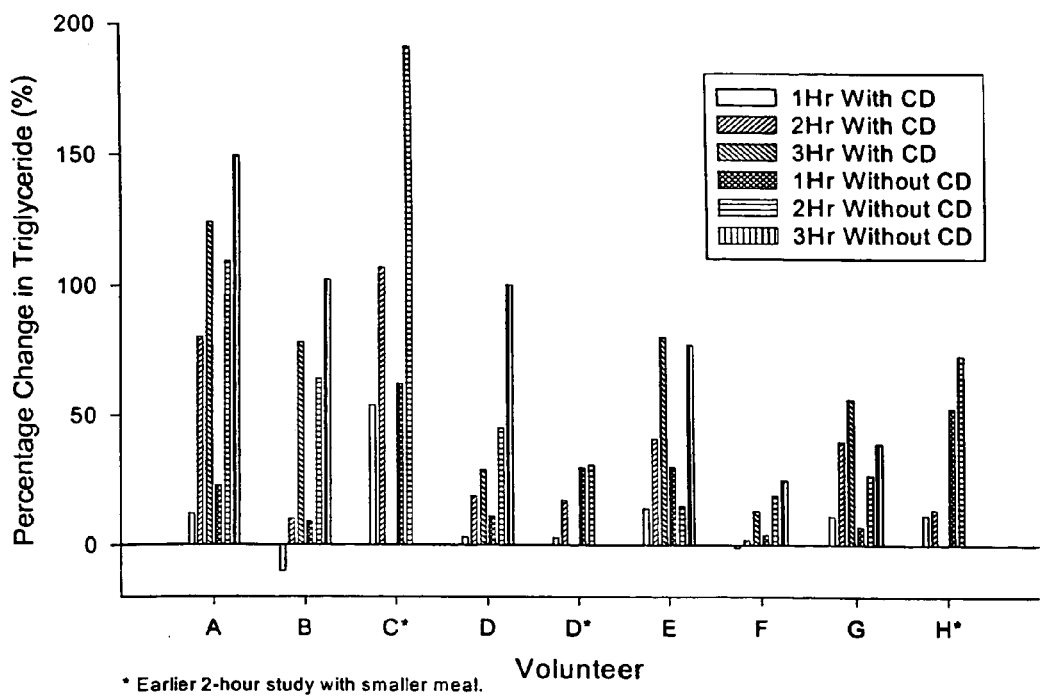
FIG. 7 depicts the serum triglyceride levels of volunteers fed a high fat breakfast following an overnight fast.

To determine the effect of α-cyclodextrin on triglyceride levels, eight volunteers were fed on two consecutive days a two-egg cheese (54 g) omelet and a milkshake containing a total of 47 g of fat after an overnight fast. On the first day the meal also contained approximately 5 g of α-cyclodextrin. Blood samples (10 ml) from each volunteer taken via an in-dwelling venous catheter immediately prior the meal (zero-time) and at 1, 2 and 3 hours after the meal was consumed and were assayed for serum triglyceride levels. The zero-time sample were used as the baseline to calculate the percentage change in blood serum triglyceride levels of the human volunteers at one, two and three hours. FIG. 7 illustrates the data collected from the volunteers. It is of note that the expected increase in serum triglyceride levels is less when the α-cyclodextrin was mixed with the food than when it is not present, although the difference failed to reach significance ($p<0.08$) due to large variation among the individuals and the small number of individuals included in this study.

FIG. 7 also contains data from three of the volunteers who had partaken in an earlier two-hour study with a smaller meal (denoted "*"). The earlier two hour study also demonstrates that the change in triglyceride levels is less when α-cyclodextrin is included in the meal.

Weight Loss Effects

Figure 8:
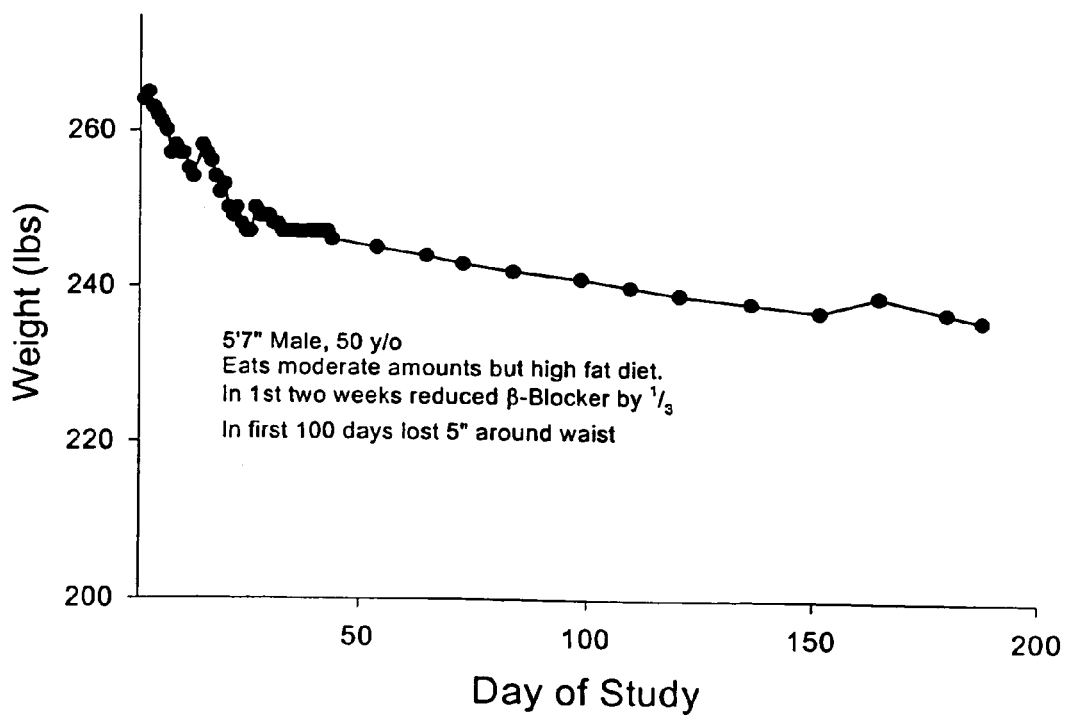
FIG. 8 depicts the change in body weight of a human volunteer over a period of approximately 6 months.

To determine if α-cyclodextrin added to a high fat diet resulted in weight loss, α-cylcodextrin was added to the high fat diet of a test subject, i.e., a 50 year old male human volunteer, five feet seven inches tall with an initial weight of 267 pounds. The α-cyclodextrin was added to the subject's diet in a proportion of one gram of α-cyclodextrin for every nine grams of fat that were estimated to be consumed by the subject. FIG. 8 demonstrates the change in the body weight of the subject over a period of 200 days, approximately 6 months. By 6 months the subject's body weight was reduced by 32 pounds. In addition to the weight loss, within the first two weeks of the study, the subject's elevated blood pressure fell to the point where he was forced to reduce his prescribed beta-blocker by one-third. His blood triglycerides were also assayed during this time and his blood serum triglyceride levels were decreased by 23% within the first month and 46% by the end of six months. The effects of the α-cyclodextrin on various parameters are set forth in Table 2.

TABLE 2

| Parameter | Baseline | 1 month | 6 months |
|---|---|---|---|
| Cholesterol (mmol/L) | 4.76 | 4.76 | 4.0 |
| HDL cholesterol (mmol/L) | 0.97 | 1.00 | 1.11 |
| Cholesterol/LDL | 4.91 | 4.76 | 4.41 |
| Triglycerides (mmol/L) | 2.76 | 2.13 | 1.50 |
| Insulin Resistance | 2.85 | 2.13 | 1.35 |
| Body Mass Index | | 39.17 | 37.27 |
| Body Fat (%) | | 33.5 | 30.0 |
| Waist (cm) | | 124 | 117 |
| Hip (cm) | | 127 | 117 |
| Dietary Energy Kcal/d | | 1,656 | 1,795 |
| Total Fat (g/d) | | 112 | 103 |
| Proportion fat (%) | | 60.9 | 51.7 |
| Total Carbohydrate (g/d) | | 56 | 84 |
| Proportion Carbohydrates (%) | | 13.5 | 18.7 |
| Total Protein (g/d) | | 106 | 133 |
| Proportion Protein (%) | | 25.6 | 29.6 |

α-cyclodextrin was also added to the diet of two additional volunteers. The α-cyclodextrin was added in a proportion such that each meal comprised about 2 g of α-cyclodextrin. Table 3 sets forth the effects of the α-cyclodextrin on reducing the levels of cholesterol, LDL, cholesterol/HDL ratio and serum triglycerides. It is of note that both of these volunteers, as well as the initial volunteer, had been and still were taking one of the statin pharmaceuticals for lowering their blood serum cholesterol. All three volunteers were taking different statins. In addition volunteer "FK" was taking 3 g/d niacin which he reduced by 50% in the first two weeks of the study because of the unpleasant side effects of this medication.

TABLE 3

| Volunteer | Period Months | Cholesterol | Cholesterol/HDL | LDL | TG |
|---|---|---|---|---|---|
| FK | 2.5 | −18.5% | −16.1% | −25.6% | −22.2% |
| JA | 6 | −10.2 | −8.8 | −15.0 | −37.5% |

Example 4

Insulin and Leptin Levels

Blood samples were taken from the two additional subjects in Example 3 at various timepoints and assayed for insulin levels and leptin levels by the method of Linco Research (St. Charles, Mo.) using human insulin and leptin radioimmune assays.

The results of this analysis, presented in Table 4, demonstrate that the reduction in levels of insulin and leptin is more than that which can be accounted for by the reduced body weight.

TABLE 4

|  | Days on diet | Body weight (lb/kg) | Insulin (uU/ml) | Leptin (ng/ml) |
|---|---|---|---|---|
| Subject 1 | 0 | 196/89.09 | 14 | 3.6 |
|  | 55 | 188/85.45 | 13 | 2.9 |
|  | 112 | 180/81.82 | 8 | 1.6 |
|  | % decrease | 5.0% | 42.9% | 55.6% |
| Subject 2 | 0 | 232/105.45 | 26 | 6.1 |
|  | 28 | 230/104.55 | 28 | 6.0 |
|  | 62 | 220.5/100.23 | 16 | 3.9 |
|  | % decrease | 5.0% | 38.5% | 36% |

Example 5

An eighteen month old, neutered male dog of unknown parentage having chronic diarrhea was de-wormed twice and placed on hypoallergenic food in an effort to control the diarrhea. However, the chronic diarrhea was not alleviated and the dog stopped eating for a day or two on two or three separate occasions.

The dog was then treated with α-cyclodextrin as follows: The dog was placed on a diet comprising a teaspoon (2.5 g) of α-cyclodextrin mixed with two cups dry food twice a day for two and one-half weeks. Based on the fat content in the food, the ratio of α-cyclodextrin to fat was about 1:9. The dog's chronic diarrhea was eliminated during this period except for an acute episode of loose stools after a day of swimming in a river but the stool has been formed ever since.

The dog was then fed an identical diet that did not comprise α-cyclodextrin for 4 days. The dog very quickly lost his appetite, self restricted his food intake by about one-half and began eating grass, grass helps to bind his stool. The diarrhea returned.

Example 6

Food Products

The amount of α-cyclodextrin incorporated into the foods of this invention is based on the amount of fat contained in the food product. The following describes a variety of conventional fat containing foods products wherein α-cyclodextrin has been added in accordance with this invention. Table 5 sets forth the total weight of the food products and the amounts of α-cyclodextrin, fat and carbohydrates in the products described in this example compared to products described in other references.

A. Chocolate Chocolate Chip Espresso Cookies

| | |
|---|---|
| 260 g | pastry flour |
| 75 g | cocoa powder |
| 3.8 g | baking powder |
| 2.8 g | salt |
| 226 g | margarine |
| 150 g | sugar |
| 180 ml (165 g) | molasses or brown sugar |
| 28 g | α-cyclodextrin |
| 5 g | vanilla extract |
| 22 g | espresso (room temperature) |
| 2 | eggs |
| 115 g | chocolate chips |

The flour, cocoa, baking powder and salt were mixed together and then the margarine, sugar, molasses (or brown sugar), α-cyclodextrin, vanilla and espresso were added to the mixture. Lightly beaten eggs were stirred into the batter and the chocolate chips were folded in. Large teaspoon-size dollops of the batter were placed on a lightly greased cookie sheet and then baked for about 15 minutes in a conventional oven or 10-12 minutes in a convection oven preheated at 375° F. The cooked cookies were cooled on a wire rack.

Most blinded tasters found that the baked cookies were indistinguishable from those prepared from the same recipe without the addition of the α-cyclodextrin. Those who detected a difference preferred those that included the α-cyclodextrin as they were described to be; richer, smoother, tastier and moister with a more pleasing texture in the mouth than the cookies without the α-cyclodextrin.

B. Honey Oatmeal Cookies

| | |
|---|---|
| 42 g | butter |
| 110 g | brown sugar |
| 85 g | honey |
| 1 | egg |
| 15 g | water |
| 58 g | flour |
| 2.5 g | salt |
| 0.75 g | baking soda |
| 81 g | rolled oats |
| 4 g | α-cyclodextrin |

In a mixer, preferably with a paddle attachment, the wet ingredients, butter, brown sugar, honey, egg and water, were mixed together. The remaining dry ingredients except for the rolled oats, were sifted together into a bowl. The rolled oats were then added to the dry ingredients. The wet and the dry ingredients were then mixed together and aliquots of the batter were deposited onto a greased cookie sheet and baked for 12-15 minutes in a conventional oven preheated to 350° F. or 8-10 minutes in a convection oven. The cooked cookies were cooled on a wire rack.

Most blinded tasters found that the baked cookies were indistinguishable from those prepared from the same recipe without the addition of the α-cyclodextrin. Those who detected a difference preferred those that included the α-cyclodextrin as they were described to be; richer, smoother, tastier and moister with a more pleasing texture in the mouth than the cookies without the α-cyclodextrin.

C. Five Layer Bars

| | |
|---|---|
| 69 g | corn flake crumbs |
| 100 g | sugar |
| 113 g | butter or margarine |

-continued

| | |
|---|---|
| 115 g | chocolate chips |
| 115 g | butterscotch chips |
| 124 g | flaked coconut |
| 63 g | chopped nuts |
| 1 can | (14 oz, 400 g) sweetened condensed milk |
| 36 g | α-cyclodextrin |

Corn flake crumbs, sugar, melted butter and 18 g α-cyclodextrin were mixed together in a 13×9×2-inch baking pan, stir together. The mixture was pressed evenly and firmly in bottom of pan to form a crust.

The chocolate chips, butterscotch chips, coconut, and chopped nuts were spread evenly in layers over the crust and 14 oz (400 g) of sweetened condensed milk mixed with 18 g of α-cyclodextrin were poured evenly over the 5 layers and then baked at 350° F. for 23 minutes or until lightly browned around edges. The product was cooled completely and cut into 24 pieces.

Most blinded tasters found that the baked bars were indistinguishable from those prepared from the same recipe without the addition of the α-cyclodextrin. Those who detected a difference preferred those that included the α-cyclodextrin as they were described to be; richer, smoother, tastier, sweeter and moister with a more pleasing texture in the mouth than the bars without the α-cyclodextrin. It is of note that sweetened condensed milk undergoes a significant change upon mixing with α-cyclodextrin. Typically sweetened condensed milk is very thick making it difficult to pour and is an unappealing off-white color. Upon mixing with the α-cyclodextrin it becomes much smoother and more fluid in nature as well as changing in appearance to a very bright white color.

D. Macaroni with Cheese

| | |
|---|---|
| 98 g | butter |
| 29 g | flour |
| 484 g | half and half cream |
| 4 g | salt |
| 0.53 g | ground white pepper |
| 6 g | chili sauce |
| 106 g | grated parmesan cheese |
| 57 g | grated cheddar cheese |
| 50 g | grated fontina cheese |
| 50 g | grated gruyere cheese |
| 450 g | macaroni |
| 3 g | minced garlic |
| 25 g | fresh bread crumbs |
| 3 g | seasoning |
| 33 g | α-cyclodextrin |
| ½ tsp | seasoning |
| 33 g | α-cyclodextrin |

29 g of flour and 33 g of α-cyclodextrin were added to 56 g of butter, melted and cooked for 3 minutes. The half and half was added slowly to the melted butter and flour mixture and then cooked with frequent stirring until thickened, about 4 to 5 minutes. The mixture was removed from the heat and the salt, pepper, hot sauce and half of the grated parmesan were added to the mixture and stirred until the cheese melted.

The macaroni was cooked in boiling water and the cooked macaroni was combined with butter and the minced garlic. The cheese mixture was added to the macaroni. The remaining cheeses were mixed and added to the macaroni mixture, the bread crumbs were layered over the macaroni and cheese and baked for 40 to 45 minutes.

Blinded tasters found that the food prepared with the α-cyclodextrin was creamier and moister than the same food prepared without the α-cyclodextrin.

TABLE 5

| | Total weight, g | Total CHO, g | Total fat, g | Added α-CD, g | α-CD as % total wt | α-CD as % of CHO | α-CD as % of fat | Kcal fat (%) | fat wt/total wt (%) | Kcal CHO (%) | CHO wt/ total wt (%) |
|---|---|---|---|---|---|---|---|---|---|---|---|
| Cheese omelet | 162 | 5 | 30 | 3.5 | 2.2% | 70% | 11.7% | 68% | 18.5% | 5% | 3.1% |
| Peanut butter | 34 (2 tsp) | 8 | 16 | 2.0 | 5.9% | 25% | 12.5% | 70% | 47% | 15% | 23.5% |
| Meatloaf | 1659 | 146 | 317 | 36 | 2.2% | 24.7% | 11.4% | 69% | 19.1% | 14% | 8.8% |
| Macaroni w/4 cheeses | 1586 | 395 | 293 | 33 | 2.1% | 8.4% | 11.3% | 51% | 18.5% | 31% | 24.9% |
| Five layer bars | 1241 | 702 | 292 | 35 | 2.8% | 5.0% | 12% | 46% | 23.5% | 49% | 56.6% |
| French-apple bread pudding[1] | 1365 | 295 | 112 | 10.5 | 0.8% | 3.6% | 9.4% | 42.4% | 8.2% | 49.6% | 21.6% |
| Honey oatmeal cookies | 492 | 308 | 48 | 3.5 | 0.7% | 1.1% | 7.3% | 24% | 9.8% | 69% | 62.6% |
| Chocolate chocolate chip expresso cookies | 1020 | 556 | 231 | 28 | 2.8% | 5.0% | 12.2% | 46% | 22.7% | 49% | 54.5% |
| Biscotti | 1323 | 870 | 108 | 12 | 0.9% | 1.4% | 11.1% | 20% | 8.2% | 71% | 65.8% |
| Butter cake Japanese application S60-94912 | 470 | 170 | 141 | 50 (CD comp)[2] | 10.6% (CD comp)[2] 3.2% α-CD | 29.4% (CD comp)[2] 8.8% α-CD | 35.5% (CD comp)[2] 10.6% α-CD | 64% | 30% | 31% | 36.2% |
| Chinese noodles Japanese application S60-94912 | 1336 | 535 | 22.15 | 300 (CD comp)[2] | 22.5% (comp)[2], 7.5% α-CD | 56.1% (CD comp)[2], 18.7% α-CD | 1364% (CD comp)[2] 454% α-CD | 7% | 1.7% (18.8% frying) | 72% | 74.9% |
| Biscuit Japanese application S60-94912 | 2015 | 1400 | 400 | 500 (CD comp)[2] | 24.8% (CD comp)[2] 7.4% α-CD | 35.7% (CD comp)[2] 10.7% α-CD | 125% (CD comp)[2] 37.5% α-CD | 45% | 19.9% | 49% | 69.5% |

[1] From Best Recipes This Side of Heaven Holy Trinity Anglican Church Cookbook Committee, Yorkton, Saskatchewan p. 172, Perksen Printers Ltd. Steinbach, Manitoba ROA 2AO CA A clear relationship exists between weight gain, obesity and a variety of pathologic disorders, e.g., diabetes, insulin resistance, cardiovascular disease, elevated blood lipid levels, sleep apnea, arthritis, certain types of cancer and elevated mortality rates (Solomon and Manson, "Obesity and mortality: a review of the epidemiological data". Am J Clin Nutr 1997;66:1044S-1050S). The total health care and lost productivity costs for obesity-related disorders reached $117 billion in 2000 (Overweight and obesity: At a glance. Office of the Surgeon General, 2001). Changes in body mass index (BMI) are reported to precede onset of diabetes (Resnick et al., "Relation of weight gain and weight loss on subsequent diabetes risk in overweight adults" *J Epidemiol Community Health* 2000;54:596-602), and for every one kg increase in body weight the prevalence of diabetes increases by 9% (Mokdad et al. "Diabetes trends in the U.S.: 1990-1998". Diabetes Care 2000;23:1278-1283). Although type II diabetes is associated with excess body weight, other metabolic abnormalities observed in obesity may contribute to the onset of Type II diabetes. Obese individuals tend to be hyperlipidemic, hyperinsulinemic and insulin resistant, all of which have been shown to increase the risk of developing Type II diabetes (Kissebah et al. Health risks of obesity. *Med Clin North Am* 1989;73:111-138; Kreisberg et al., Insulin secretion in obesity. *N Engl J Med* 1967;276:314-319, and; Olefsky J. Insulin resistance and insulin action: an in vitro and in vivo perspective. *Diabetes* 1981;30:148-162). Therefore, a reduction in the severity of any of these abnormalities will also reduce the risk of developing Type II diabetes. The products of this invention have organoleptic properties desired by consumers and also promote weight loss and other health benefits.

We claim:

1. A method for reducing the cholesterol/HDL ratio in a subject comprising administering to a subject in need thereof an amount of α-cyclodextrin wherein the amount of α-cyclodextrin administered to said subject and fat ingested daily by said subject is in a ratio of about 1:20 to about 1:3 w/w, and wherein said amount of α-cyclodextrin is sufficient to reduce the cholesterol/HDL ratio in said subject.

2. The method of claim 1, wherein the α-cyclodextrin is administered in a form selected from the group consisting of a tablet, powder, capsule, liquid and confection.

3. The method of claim 1, wherein the α-cyclodextrin is administered to the subject in the form of a consumable farinaceous food product comprising α-cyclodextrin and fat, wherein said food product has a ratio of α-cyclodextrin to fat of 1:20 w/w to about 1:3 w/w of said food product and wherein said food product comprises less than about 9% w/w total cyclodextrin.

4. The method of claim 1 wherein about 500 mg to 33 g of α-cyclodextrin is administered to the subject in need thereof daily to reduce the cholesterol/HDL ratio.

5. The method of claim 1 wherein the α-cyclodextrin is administered to the subject in the form of a consumable non-farinaceous food product comprising complexes of ☐ α-cyclodextrin and fat, wherein said non-farinaceous food product has a ratio ☐ α-cyclodextrin to fat of 1:20 w/w to about 1:3 w/w of said food product.

\* \* \* \* \*